(12) United States Patent
Merzenich et al.

(10) Patent No.: US 7,773,097 B2
(45) Date of Patent: *Aug. 10, 2010

(54) VISUAL EMPHASIS FOR COGNITIVE TRAINING EXERCISES

(75) Inventors: Michael M. Merzenich, San Francisco, CA (US); Peter B. Delahunt, San Mateo, CA (US); Joseph L. Hardy, Richmond, CA (US); Henry W. Mahncke, San Francisco, CA (US); Donald Richards, Lagunitas, CA (US)

(73) Assignee: Posit Science Corporation, San Francisco, CA (US)

( * ) Notice: Subject to any disclaimer, the term of this patent is extended or adjusted under 35 U.S.C. 154(b) by 831 days.

This patent is subject to a terminal disclaimer.

(21) Appl. No.: 11/611,318

(22) Filed: Dec. 15, 2006

(65) Prior Publication Data

US 2008/0084427 A1   Apr. 10, 2008

Related U.S. Application Data

(60) Provisional application No. 60/828,316, filed on Oct. 5, 2006.

(51) Int. Cl.
*G09G 5/00* (2006.01)
*G09B 19/00* (2006.01)
*G06K 9/00* (2006.01)

(52) U.S. Cl. .................. 345/619; 382/165; 382/181; 434/236

(58) Field of Classification Search .............. 382/165; 345/619; 434/236
See application file for complete search history.

(56) References Cited

U.S. PATENT DOCUMENTS 4,971,434 A   11/1990 Ball 5,801,810 A   9/1998 Roenker (Continued)

FOREIGN PATENT DOCUMENTS

DE   69529054   8/2003

(Continued)

OTHER PUBLICATIONS

Su, Sara L., Fredo Durand, and Maneesh Agrawala. De-Emphasis of Distracting Image Regions Using Texture Power Maps (2005): 1-12. DSpace@MIT : De-Emphasis of Distracting Image Regions Using Texture Power Maps. Apr. 12, 2005. Web. Sep. 21, 2009. <http://dspace.mit.edu/handle/1721.1/30537>.*

(Continued)

*Primary Examiner*—Kee M Tung
*Assistant Examiner*—Robert Craddock
(74) *Attorney, Agent, or Firm*—James W. Huffman

(57) ABSTRACT

Computer-implemented method for enhancing cognition of a participant using visual emphasis. One or more scenes are provided and are available for visual presentation to the participant, each scene having a background and at least one foreground object. A scene is visually presented to the participant with a specified visual emphasis that enhances visual distinction of the at least one foreground object with respect to the background, where the foreground object(s) and/or the background are modified or selected to achieve the specified visual emphasis. The participant is required to respond to the scene, and a determination made as to whether the participant responded correctly. The visual emphasis may be modified based on whether or not the participant responded correctly a specified number of times. The presenting, requiring, and determining (and possibly the modifying) are repeated in an iterative manner to improve the participant's cognition.

35 Claims, 14 Drawing Sheets

U.S. PATENT DOCUMENTS

| | | |
|---|---|---|
| 6,328,569 B1 | 12/2001 | Jenkins et al. |
| 6,364,486 B1 | 4/2002 | Ball et al. |
| 6,464,356 B1 | 10/2002 | Sabel et al. |
| 6,599,129 B2 | 7/2003 | Jenkins et al. |
| 7,367,675 B2 | 5/2008 | Maddalena et al. |
| 2003/0201982 A1* | 10/2003 | Iesaka .................. 345/168 |
| 2005/0175972 A1 | 8/2005 | Goldman et al. |
| 2005/0213033 A1* | 9/2005 | Sabel .................. 351/203 |
| 2007/0166675 A1 | 7/2007 | Atkins et al. |
| 2007/0166676 A1 | 7/2007 | Bird et al. |
| 2007/0218439 A1 | 9/2007 | Delahunt et al. |
| 2007/0218440 A1 | 9/2007 | Delahunt et al. |
| 2007/0218441 A1 | 9/2007 | Delahunt et al. |
| 2007/0293732 A1 | 12/2007 | Delahunt et al. |

FOREIGN PATENT DOCUMENTS

| | | |
|---|---|---|
| EP | 00502984 | 12/1992 |
| EP | 1069855 | 8/2001 |
| WO | WO9952419 | 10/1999 |
| WO | WO03065964 | 8/2003 |

OTHER PUBLICATIONS

Phipps, Joanna A., Andrew J. Zele, Trung Dang, and Algis J. Vingrys. "Fast psychophysical procedures for clinical testing." Procedures for clinical testing (2001): 264-69. QUP ePrints. May 4, 2007. Web. Sep. 21, 2009. <http://eprints.qut.edu.au/7481/>. hereafter known as "Phipps".*

Sekuler et al. "Visual localization: age and practice." Optical Society of America. vol. 3, No. 6. Jun. 1986. pp. 864-867.

Ball et al. "Effects of Cognitive Training Interventions With Older Adults: A Randomized Controlled Trial." American Medical Association. Nov. 13, 2002. vol. 288, No. 18. pp. 2271-2281.

* cited by examiner

Enhanced

Standard

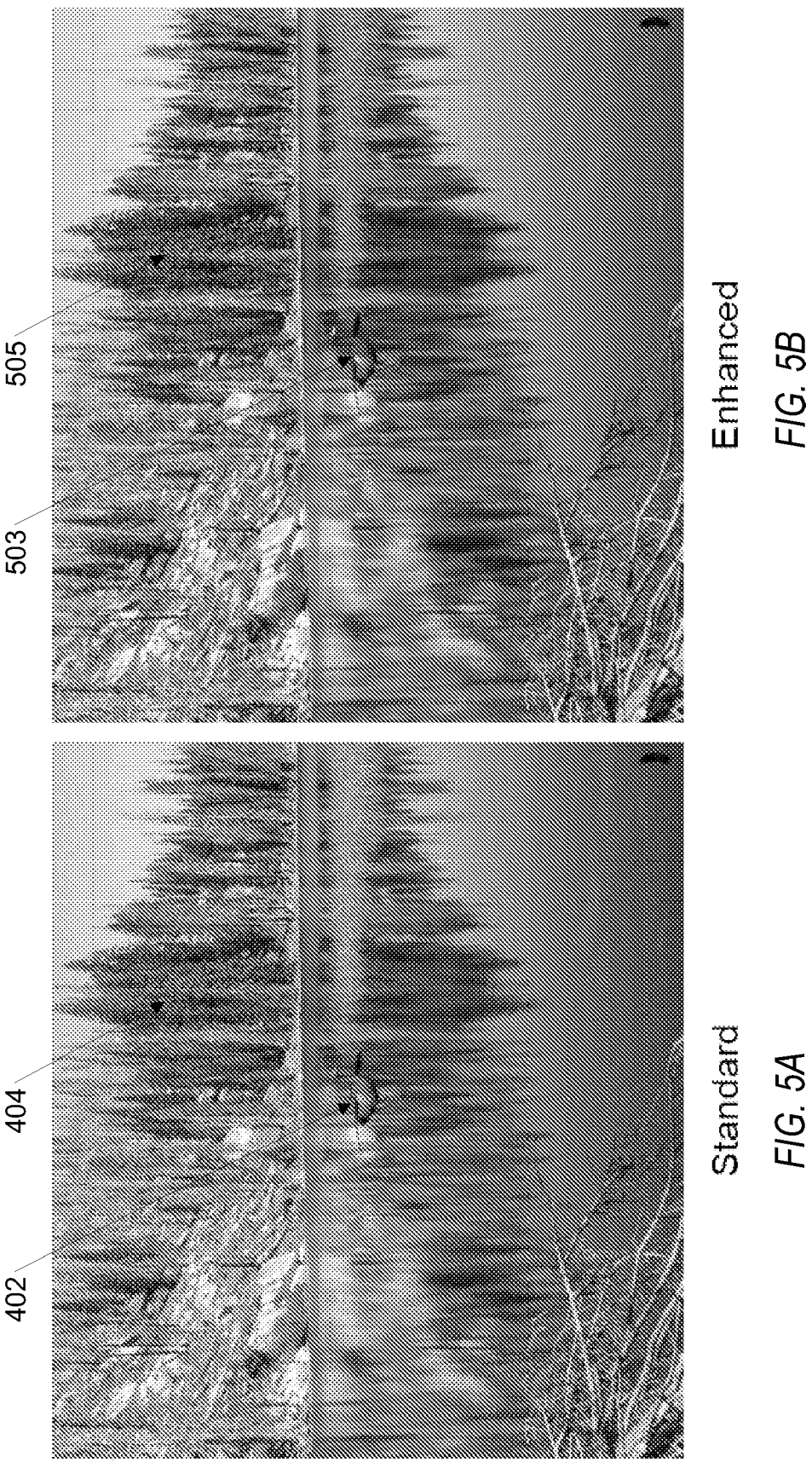
FIG. 5A Standard
FIG. 5B Enhanced

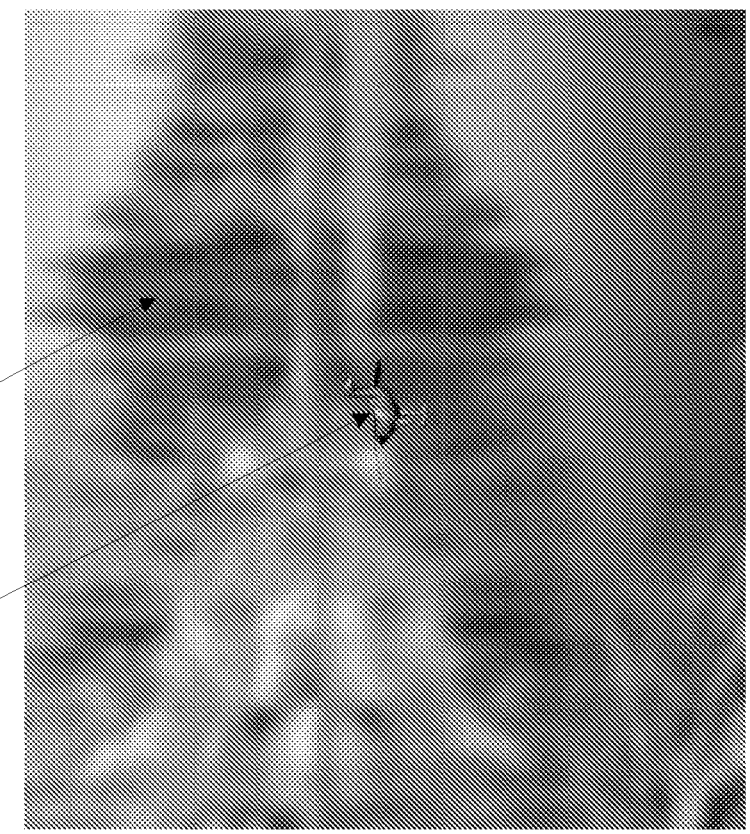
FIG. 6B Enhanced
FIG. 6A Standard

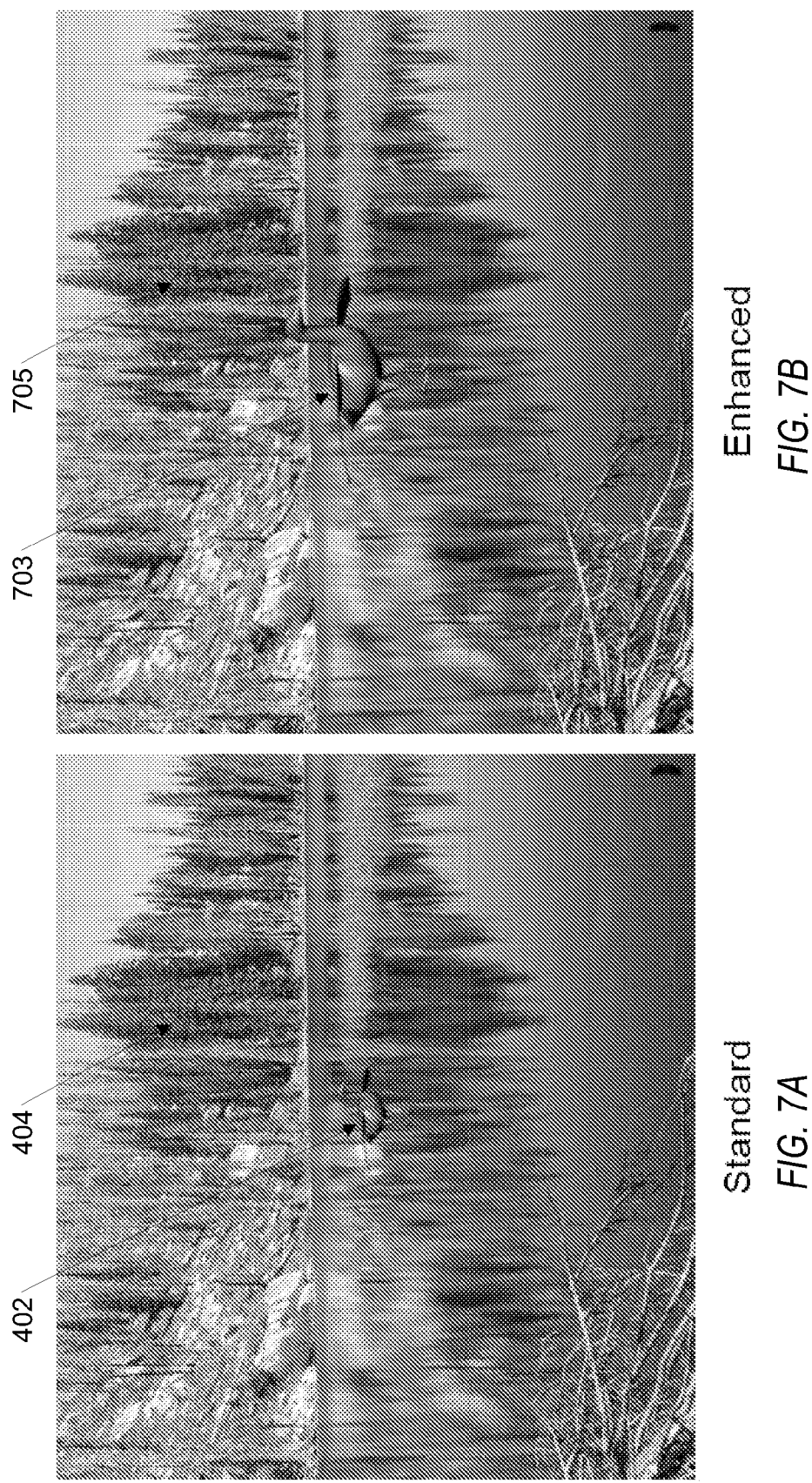
FIG. 7A Standard
FIG. 7B Enhanced

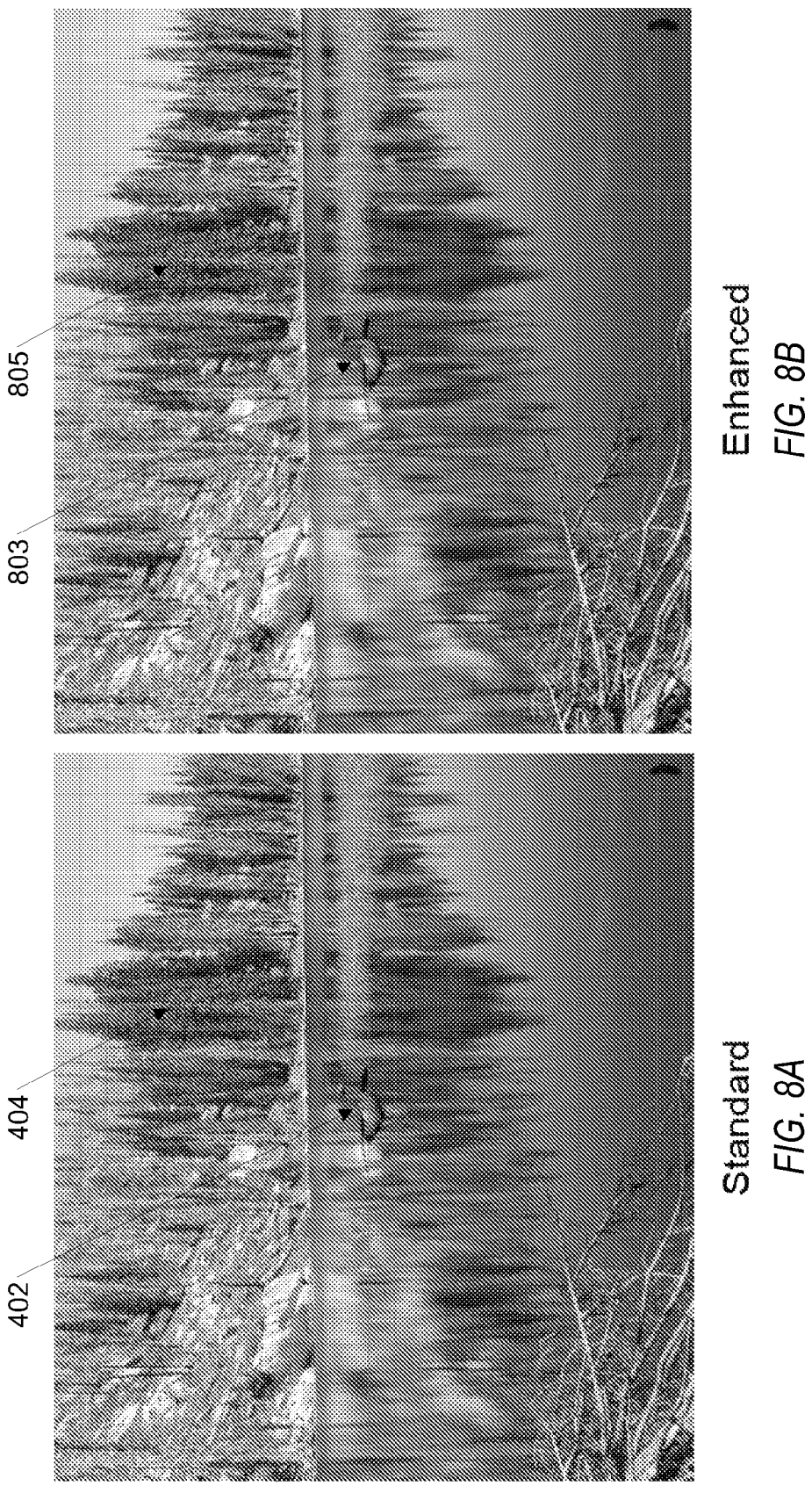
FIG. 8B Enhanced
FIG. 8A Standard

Enhanced

Standard

VISUAL EMPHASIS FOR COGNITIVE TRAINING EXERCISES

CROSS REFERENCE TO RELATED APPLICATION(S)

This application claims the benefit of the following US Provisional Patent Applications, which are incorporated herein in their entirety for all purposes:

| Ser. No. | Filing Date: | Title: |
| --- | --- | --- |
| 60/828,316 | Oct. 5, 2006 | VISUAL EMPHASIS |

The following applications are related to the present application:

| | | |
| --- | --- | --- |
| * * * | * * * | COGNITIVE TRAINING USING VISUAL SWEEPS |
| * * * | * * * | COGNITIVE TRAINING USING VISUAL SEARCHES |
| * * * | * * * | COGNITIVE TRAINING USING MULTIPLE OBJECT TRACKING |
| * * * | * * * | COGNITIVE TRAINING USING FACE-NAME ASSOCIATIONS |
| * * * | * * * | COGNITIVE TRAINING USING EYE MOVEMENT |
| * * * | * * * | COGNITIVE TRAINING USING VISUAL STIMULI |

FIELD OF THE INVENTION

This invention relates in general to the use of brain health programs utilizing brain plasticity to enhance human performance and correct neurological disorders, and more specifically, to computer-based cognitive training with visual stimuli using visual emphasis.

BACKGROUND OF THE INVENTION

Some computer-based cognitive training exercises use audible stimuli to invoke a response from a participant, where a sound, such as a word or phoneme, is presented, and the participant is required to respond in some way, e.g., by identifying the sound. In some of these exercises, the stimulus sounds may be presented in various ways to affect the ease or difficulty with which the sounds may be perceived, e.g., by modulating the sound's volume, speed of delivery, and so forth. However, these techniques are only used in auditory-based training.

Thus, improved systems and methods for cognitive training are desired.

SUMMARY

Various embodiments of a system and method are presented for enhancing cognition in a participant, utilizing a computing device to present visual stimuli for training, and to receive responses from the participant.

One or more scenes, each having a background and at least one foreground object, may be provided, where the one or more scenes are available for visual presentation to the participant. For example, the scenes may be stored on a memory medium of the computing device, on a memory medium coupled to the computing device, e.g., over a network, etc. The scenes may be stored as complete scenes, or in separate parts, e.g., backgrounds and foreground objects, and assembled as needed, e.g., for visual presentation to the participant, described below. Note that the backgrounds and foreground objects may be of any type desired, i.e., may have a wide range of complexity, subject matter, and so forth. For example, in some scenes, the background may be a blank visual field, while in others the background may be visually rich in detail, color, etc. Similarly, the at least one foreground object may be singular, or may include a plurality of foreground objects, of any level of complexity desired. For example, foreground objects included in the scenes may include simple objects, e.g., geometrical objects, such as circles, squares, etc., of various colors, sizes, and so forth, or more complex objects, such as images of people, faces, animals, plants, products, machines, buildings, or other structures, among others. In other words, the scenes may include images of any type desired.

A scene from the one or more scenes may be visually presented to the participant with a specified visual emphasis that visually distinguishes the at least one foreground object with respect to the background. Said another way, visually presenting the scene may include visually presenting the at least one foreground object and/or the background with a specified visual emphasis that visually distinguishes the foreground object(s) with respect to the background. This visual emphasis may facilitate more robust encoding of the visual representation and easier perception by the participant of the foreground object(s) against the background.

In some embodiments, this visually presenting with visual emphasis may include modifying the visual emphasis of the at least one foreground object and/or the background to achieve the specified visual emphasis. In other words, the at least one foreground object and/or the background may be graphically processed, such as described above in detail, to emphasize or enhance visual distinction between the foreground object(s) and the background. Thus, for example, some standard image (i.e., foreground object(s) and/or background) may be manipulated or processed "on demand" to achieve the specified visual emphasis.

In other embodiments, the visually presenting with visual emphasis may include selecting the at least one foreground object and/or the background in accordance with the specified visual emphasis to enhance visual distinction of the at least one foreground object with respect to the background. In other words, the at least one foreground object and/or the background may be selected from a set or collection of foreground objects and/or backgrounds that includes foreground objects and/or backgrounds of varying visual emphasis, where the at least one foreground object and/or the background are selected based on the desired or specified degree of visual emphasis. In some embodiments, the set or collection of foreground objects and/or backgrounds may be created by modifying one or more basis or standard foreground objects and/or backgrounds, e.g., according to one or more of the visual emphasis techniques described below, and/or by accumulating or collecting images that happen to include the various levels of visual emphasis. This distinguishability of foreground object(s) with respect to the background of a scene may be referred to as the salience of the foreground object(s). Said another way, the visual emphasis techniques described herein may operate to make foreground objects more noticeable or obvious to the participant.

There are a variety of ways the foreground object(s) and/or the background may be modified to visually emphasize the distinctions between them, e.g., to effect visual emphasis for the scene. For example, in various embodiments, the specified visual emphasis may specify one or more of: luminance contrast of the at least one foreground object and/or the background, chromatic contrast of the at least one foreground object and/or the background, spatial frequency of the at least one foreground object and/or the background, size of the at least one foreground object and/or features in the background, flashing the at least one foreground object, moving the at least one foreground object with respect to the background, texture of the at least one foreground object and/or the background, opacity of the at least one foreground object and/or the background, positioning the at least one foreground object with respect to one or more other foreground objects and/or with respect to one or more features of the background, and/or attentional effects of one or more distracting features of the background, among others. In other words, any of the above effects, including any combination of them, may be increased (or decreased) to achieve a specified visual emphasis for the scene.

Of course, other means of enhancing visual emphasis or distinction of the foreground object(s) with respect to the background of a scene may be used as desired. For example, if there are features or objects in the background that are confusable with the foreground object(s), these features or objects may be modified to decrease the confusability, e.g., by removing or replacing the features or objects from the scene, changing their coloration, or otherwise making them less noticeable to the participant. As one example, in a scene where a duck is displayed against a background that includes a forest scene containing chromatic, luminance, spatial frequency and texture content similar to that of the duck, effectively camouflaging the duck, may be replaced by a scene that is quite dissimilar in visual content to the duck, e.g., a clear blue sky. Note that the above techniques are meant to be exemplary only, and that other approaches for visual emphasis may be used as desired.

Note further that in some embodiments, two or more the above-described modifications, among others, may be made in conjunction. In other words, in various embodiments, any of the various visual emphasis techniques may be used singly or in combination to enhance or emphasize visual distinction of the foreground object(s) with respect to the background.

The participant may be required to respond to the scene. For example, in various embodiments, the participant may be required to respond based on information gleaned from foreground objects in the scene, and/or features in the background, e.g., depending on the particular cognitive exercise being performed. In various embodiments, the participant may respond to the scene in any of a variety of ways, including, for example, clicking on objects in the scene with a mouse, clicking on icons or buttons in a graphical user interface (GUI) (possibly within which the scene is displayed), clicking on specified regions in the visual field, pressing keys on a keyboard coupled to the computing device, using voice recognition to enter responses, responding via a touch screen, e.g., by touching objects in the scene, buttons in the GUI, etc., among others. Of course, the particular response required of the participant may depend upon the specific cognitive training being performed, e.g., may depend on the specific cognitive training exercise being performed. Note that in various embodiments, any means for responding to the scene may be used as desired, the above being exemplary only.

A determination may be made as to whether the participant responded correctly. The response, and/or the correctness/incorrectness of the response, may be recorded. In some embodiments, an indication, e.g., a graphical and/or audible indication, may be provided to the participant indicating the correctness or incorrectness of the participant's response, e.g., a "ding" or a "thunk" may be played to indicate correctness or incorrectness, respectively, and/or points may be awarded (in the case of a correct response). Of course, any other type of indication may be used as desired, e.g., graphical images, animation, etc.

The above visually presenting, requiring, determining, may compose a trial in the exercise or task, and may be repeated one or more times in an iterative manner to improve the participant's cognition, e.g., visual memory, attention, speed and/or processing skills. In other words, a plurality of trials may be performed as described above, preferably using a plurality of different scenes, although multiple trials may certainly be directed to a scene as desired. In some embodiments, multiple trials may be performed under each of a plurality of conditions, e.g., using different types of scenes, with scenes visually presented with different visual emphasis, for different durations, and so forth.

In some embodiments, the specified visual emphasis may be modified based on the determining, e.g., based on whether or not the participant responded correctly a specified number of times (e.g., 1, 10, 40, etc.). Similar to above, modifying the specified visual emphasis may include one or more of: modifying the visual emphasis of the at least one foreground object and/or the background to modify the visual emphasis, and/or selecting a different at least one foreground object and/or a different background for the scene to modify the visual emphasis.

Thus, the repeating may include adjusting or modifying the (amount or degree of) visual emphasis based on the determining. In some embodiments, for any given visual emphasis technique described herein, the amount of the modification may be adjusted based on the participant's performance. Thus, for example, using the size modification of a foreground object as an example, if the participant responds incorrectly in a trial, then the size of the foreground object may be increased for the next trial; and if the participant responds correctly in a trial, the size of the foreground object may be decreased for the next trial. Thus, modifying the visual emphasis may include adjusting the degree of visual emphasis based on any of the above visual emphasis techniques, e.g., increasing or decreasing the amount of any particular technique(s).

As noted above, in various embodiments, the various visual emphasis techniques described above may be used singly or in conjunction. Thus, in addition to, or instead of, the above approach to modifying the visual emphasis, in embodiments where the at least one foreground object and/or the background are modified by (or selected in accordance with) one or more of the above visual emphasis techniques, modifying the visual emphasis, e.g., modifying visual aspects of foreground object(s) and/or the background, may include applying or using one or more additional or less of the techniques, based on the participant's response(s), e.g., to make trials easier or more difficult. Thus, for example, if the scene were presented with a specified visual emphasis based on luminance and chromatic contrast, then, based on the participant's response, the number and/or type of visual emphasis techniques applied to the scene may be changed. For example, to make trials easier, the visual emphasis may be increased, e.g., by further applying a spatial frequency emphasis, e.g., increasing the sharpness of the foreground object (in addition to the luminance and chromatic contrast) thereby making the stimulus (the scene) more easily perceived, and conversely, to increase the difficulty of trials, then the visual emphasis may be decreased, e.g., by removing one (or more) of the luminance contrast or chromatic contrast emphasis, thereby making the stimulus (the scene) more difficult to perceive. In other words, decreasing the visual emphasis may include ceasing to perform at least one of the one or more modification techniques, thereby making the next trial more difficult.

Described more specifically, in embodiments where modifying the visual emphasis includes modifying one or more of: luminance contrast of the at least one foreground object and/or the background, color contrast of the at least one foreground object and/or the background, spatial frequency of the at least one foreground object and/or the background, size of the at least one foreground object and/or features in the background, flashing the at least one foreground object, moving the at least one foreground object with respect to the background, texture of the at least one foreground object and/or the background, positioning the at least one foreground object with respect to one or more other foreground objects and/or with respect to one or more features of the background, and/or reducing attentional effects of one or more distracting features of the background, increasing the visual emphasis may include increasing one or more others of the luminance contrast, color contrast, spatial frequency, size, flashing, moving, texture, positioning, or reducing attentional effects, thereby making the next trial less difficult, and decreasing the visual emphasis may include ceasing to modify at least one of the one or more of: luminance contrast, color contrast, spatial frequency, size, flashing, moving, texture, positioning, or reducing attentional effects, thereby increasing the difficulty of trials.

In yet another embodiment, the visual emphasis of the scene may be modified by exchanging or switching out an applied visual emphasis technique, e.g., color or chromatic contrast, with another visual emphasis technique, e.g., movement of the foreground object(s), with the presumption that various of the visual emphasis techniques described herein may differ in the perceptual effects they have with respect to the participant.

Thus, in some embodiments, the number of modification techniques brought to bear on the scene may change based on whether the visual emphasis is to be increased or decreased.

In preferred embodiments, the visual emphasis of the scene may be determined by the stage of training that a participant is in, which itself may be based on the number of trials the participant has performed correctly. For example, at the beginning of a training program, scenes may be presented with a high level of visual emphasis, i.e., with a specified high degree of one or more of the visual emphasis aspects or attributes described above (e.g., luminance or chromatic contrast, spatial frequency, size, etc.), to engage the participant, and to facilitate easier perception of foreground objects against backgrounds. As the participant progresses, the scenes may be presented with lower levels of visual emphasis.

For example, the degree of visual emphasis may be determined by the participant's cumulative success or progress in the exercise, e.g., beginning with high visual emphasis scenes, when the participant has responded correctly some specified number of times, i.e., has correctly performed the specified number of trials, the specified visual emphasis may be decreased. Each time the participant has correctly responded the specified number of times (or a different specified number of times), the specified visual emphasis may be decreased again, and so forth, until the scenes are substantially un-emphasized, or even de-emphasized. In other words, the repeating may include beginning with scenes of higher visual emphasis, and the method may further include decreasing the visual emphasis if the participant responds correctly a specified number of times, i.e., the visual emphasis levels may be changed (decreased) after a specified number of correct responses.

Thus, as the participant correctly performs increasing numbers of trials, the visual emphasis of the presented scenes may decrease. There may be a specified number of levels (e.g., 5), where the participant progresses through the levels from highest emphasis to lowest emphasis.

In other embodiments, the visual emphasis of the scene for the subsequent trial may be modified or adjusted depending on whether the participant responded correctly or incorrectly for the trial. For example, in one embodiment, if the scene were presented with a specified visual emphasis, i.e., with a specified degree of one or more of the visual emphasis aspects or attributes described above (e.g., luminance or chromatic contrast, spatial frequency, size, etc.), then, based on the participant's response, the degree of visual emphasis applied to the scene may be modified or changed. For example, if the participant responded incorrectly, then the visual emphasis may be increased, i.e., one or more of the aspects or attributes described above may be increased, thereby making the stimulus (the scene) more easily perceived, and conversely, if the participant responded correctly, then the visual emphasis may be decreased, i.e., one or more of the aspects or attributes described above may be decreased, thereby making the stimulus (the scene) more difficult to perceive.

In one embodiment, visually presenting the scene may include visually presenting the scene at a specified stimulus intensity. As used herein, the term "stimulus intensity" refers to an adaptable or adjustable attribute of the scene or its presentation that may be modified or adjusted to make trials more or less difficult. The above-described adjusting of the visual emphasis may compose (or include, or result in) adjusting the stimulus intensity. In other words, by adjusting the visual emphasis, the stimulus intensity of the scene may be adjusted or modified. Said another way, in some embodiments, the stimulus intensity may be or include the visual emphasis. In preferred embodiments, adjusting the stimulus intensity may be performed using a maximum likelihood procedure, such as, for example, a QUEST (quick estimation by sequential testing) threshold procedure, and/or a ZEST (zippy estimation by sequential testing) threshold procedure, described below, whereby threshold values for the stimulus intensity may be determined based on the participant's performance.

In some embodiments, adjusting the stimulus intensity may include adjusting the stimulus intensity (e.g., the visual emphasis) to approach and substantially maintain a specified success rate for the participant, e.g., using a single stair maximum likelihood procedure. Moreover, the repeating may include assessing the participant's performance a plurality of times during the repeating, e.g., using a dual stair maximum likelihood procedure (e.g., QUEST or ZEST). In other words, not only may the stimulus intensity (e.g., the amount of modification) be adjusted on a per trial basis based on the participant's performance, but the participant's performance may be assessed periodically during the exercise, e.g., before, one or more times during, and after the exercise. Thus, the repeating may include performing threshold assessments in conjunction with, or as part of, the exercise.

Other features and advantages of the present invention will become apparent upon study of the remaining portions of the specification and drawings.

BRIEF DESCRIPTION OF THE DRAWINGS

FIGS. 5A and 5B respectively illustrate a standard scene, and an scene with enhanced color contrast, according to one embodiment;

FIGS. 6A and 6B respectively illustrate a standard scene, and an scene with enhanced spatial frequency contrast, according to one embodiment;

FIGS. 7A and 7B respectively illustrate a standard scene, and an scene with enhanced size contrast, according to one embodiment;

FIGS. 8A and 8B respectively illustrate a standard scene, and an scene with a flashing target, according to one embodiment;

DETAILED DESCRIPTION

Figure 1:
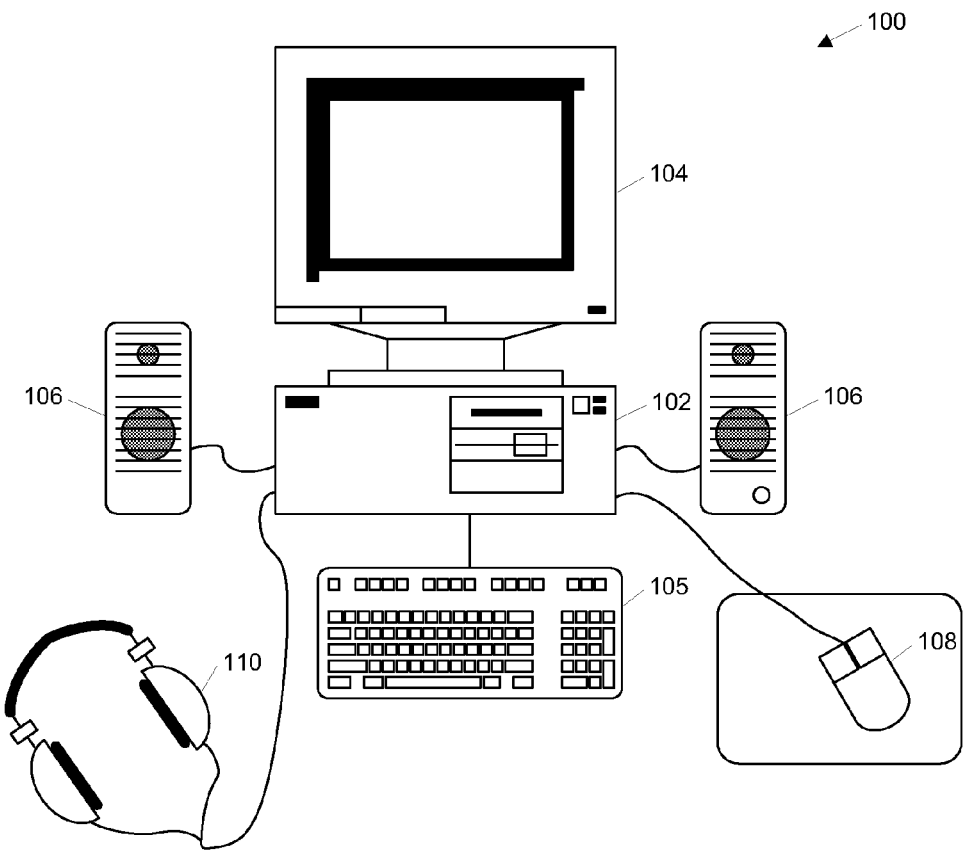
FIG. 1 is a block diagram of a computer system for executing a program according to some embodiments of the present invention.

Referring to FIG. 1, a computer system 100 is shown for executing a computer program to train, or retrain an individual according to the present invention to enhance cognition, where the term "cognition" refers to the speed, accuracy and reliability of processing of information, and attention and memory, and where the term "attention" refers to the facilitation of a target and/or suppression of a non-target over a given spatial extent, object-specific area or time window. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. In some embodiments, the speakers 106 and the headphones 110 may provide auditory prompting and feedback to the subject during execution of the computer program. The mouse 108 allows the subject to navigate through the computer program, and to select particular responses after visual or auditory prompting by the computer program. The keyboard 105 allows an instructor to enter alphanumeric information about the subject into the computer 102. Although a number of different computer platforms are applicable to the present invention, embodiments of the present invention execute on either IBM compatible computers or Macintosh computers, or similarly configured computing devices such as set top boxes, PDA's, gaming consoles, etc.

Figure 2:
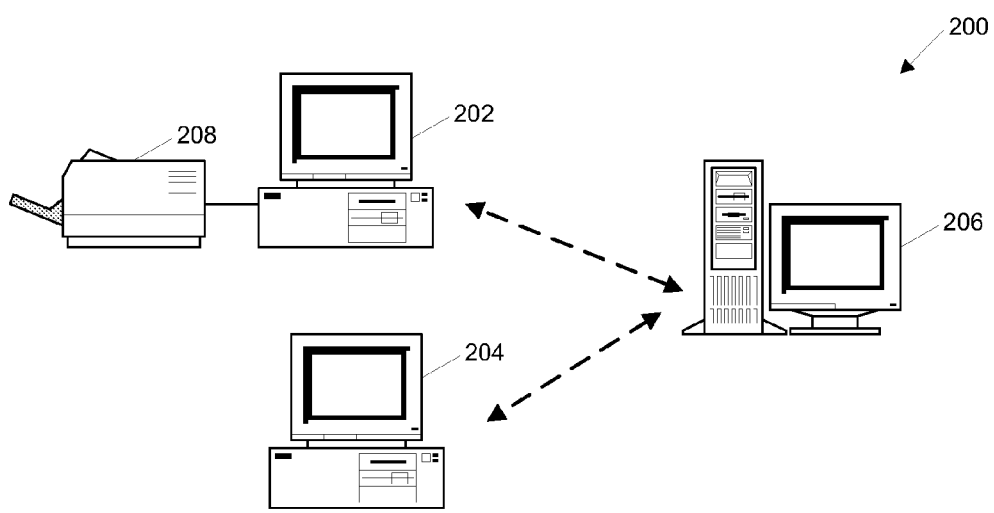
FIG. 2 is a block diagram of a computer network for executing a program according to some embodiments of the present invention.

Now referring to FIG. 2, a computer network 200 is shown. The computer network 200 contains computers 202, 204, similar to that described above with reference to FIG. 1, connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can review the information and can then download configuration and control information pertaining to a particular subject, back to the subject's computer 202, 204.

Visual Emphasis

Age-related changes cause neural systems to respond more slowly and less robustly to preferred visual stimuli than they once did. In large part these changes are due to plastic reorganization of network properties that are locally adaptive, resulting in relatively unimpaired performance under a limited and specific range of environmental stimulation encountered by the aging organism. However, these changes are generally globally maladaptive, with simple task performance, such as central foveal detection, being relatively maintained at the cost of more complex and challenging visual tasks, such as peripheral object identification.

In order to renormalize visual processing in a global sense, the efficiency of mechanisms involved in complex, speeded task performance must be improved. In order to drive positive plasticity in these systems to improve their speed, accuracy, and overall function, slow and poorly tuned neurons and neural networks need to be strongly and coherently activated in the initial phases of training in a fashion that will engage these plastic mechanisms in a robust manner. In the context of adaptive visual training, i.e., training with visual stimuli, this effect can be elicited by initially strongly "emphasizing" the visual scene. As used herein, the term "visual emphasis" generally refers to creation of a combination of a target stimulus and background stimulus, where one or both stimuli have been individually modified to have visual properties specifically chosen to drive cortical neurons strongly and coherently, and whose combination is specifically chosen to further enhance the overall configuration's ability to drive cortical neurons strongly and coherently. In other words, visual emphasis refers to image modification or manipulation that serves to increase the distinguishability of foreground objects, e.g., with respect to the background. Embodiments of the visual emphasis techniques described below are specifically designed to engage these neural mechanisms in a fashion that will robustly engage them and drive positive brain plasticity that leads to faster, more finely tuned processing.

There are several aspects or dimensions along which stimuli may be manipulated to create the emphasis levels. Some dimensions may be described with respect to the objects of interest in a scene, i.e., foreground objects, some with respect to the background of a scene, and some with respect to object/background relations. In some embodiments, the manipulations described herein may occur at two levels; the first level being the a priori level of stimulus selection and artistic design. In other words, the stimuli may be illustrated, animated or selected based on the principles described herein. The second level is the post hoc level of post-processing manipulations. Each manipulation may map to a corresponding image-processing algorithm. Commercially available programs such as Photoshop®, provided by Adobe Systems Incorporated, implement many of these algorithms. Moreover, many of these algorithms may be implemented using image processing packages such as those available in Matlab®, provided by The MathWorks. Of course, any other means for performing the image processing or manipulations described herein may be used as desired. Note that the appropriate application of visual emphasis manipulations may depend on the visual task. Not all dimensions of emphasis may apply in all cases.

Below are described exemplary aspects of visual stimuli that may be manipulated for visual emphasis. It should be noted, however, that the aspects listed are meant to be exemplary only, and are not intended to limit the visual aspects used for visual emphasis to any particular set or type of visual attributes.

Foreground Objects

The following visual attributes or aspects relate to foreground objects in a scene, i.e., objects of interest.

Spatial frequency: As used herein, and as is well known to those of skill in the imaging arts, "spatial frequency" refers to the level of graphical detail or sharpness of an image. An object that has been manipulated to have a relatively large proportion of high spatial frequency information is said to be sharpened. When the converse manipulation is made, i.e., increasing the relative amount of low spatial frequency information, the object is said to be blurred. Thus, at high levels of visual emphasis, objects may be sharpened. The increased high-spatial frequency information may strongly activate neural mechanisms in the cortex that are under-stimulated, while creating a salient contrast from the background. In other words, the object may become more distinct with respect to the background. Conversely, as the visual emphasis is decreased to low levels, the objects may become somewhat blurred, creating a more photo-realistic effect by simulating natural atmospheric scattering and optical defocus, and reducing the spatial frequency gradient cue to object/background segregation. In other words, the object may become less distinct with respect to the background.

Internal luminance contrast: As used herein, "luminance contrast" refers to the range of luminance or brightness values of pixels in an image. Stimuli with a high degree of overall (e.g., root-mean-squared) internal luminance contrast may drive impaired visual processors more strongly than stimuli with low internal luminance contrast. Neural mechanisms that are impaired or poorly tuned may be activated by high luminance contrast stimuli to the same degree that normally functioning neural mechanisms are activated by low to medium luminance contrast stimuli. This strong engagement may drive differential responses in mechanisms tuned to the relevant stimulus dimension in the object. At the high levels of emphasis, the internal luminance contrast may be made artificially high by increasing the root-mean-squared luminance contrast of the object. At lower levels, luminance contrast may be reduced, e.g., slightly below the nominal baseline level for the object.

Internal chromatic contrast: As used herein, chromatic or color contrast refers to the range of color or hue saturation values of pixels in an image. Visual cortical neurons are tuned to chromatic contrast as well as luminance contrast, and so increasing the chromatic contrast internal to the object may engage a partially overlapping distribution of neural mechanisms to those preferentially affected by increasing internal luminance contrast. Moreover, the effect of increasing both luminance contrast (see above) and chromatic contrast simultaneously is synergistic. At high levels of visual emphasis, the internal chromatic contrast may be made artificially high by increasing the root-mean-squared chromatic contrast of the object. At lower levels of visual emphasis, chromatic contrast may be reduced, e.g., to slightly below the nominal baseline level for the object.

Background

The following visual attributes or aspects relate to a background in a scene. Note that since visual emphasis refers to increasing the visual distinction or distinguishability of foreground objects with respect to backgrounds, foreground and background operations for visual emphasis may be conversely related, since increasing a background attribute may have substantially the same distinguishing effect as decreasing the foreground attribute, and vice versa.

Spatial frequency: At high levels of emphasis (for the scene), the low spatial frequency content of the background may be increased relative to the high spatial frequency content (i.e., the background may be blurred), thus making the foreground object(s) appear sharper in contrast. Conversely, as the visual emphasis level is decreased, the blurring of the background may be reduced until, at the final stage, no spatial frequency manipulation is performed.

Internal luminance contrast: At high levels of visual emphasis, the luminance contrast of the background elements may reduced, thereby making the foreground object(s) appear to have more luminance contrast in contrast to the background. At low levels of visual emphasis, the luminance contrast of the background may be increased until, by the final level, the luminance contrast may be set at a naturalistic level, i.e., no modification.

Internal chromatic contrast: At the high levels of emphasis, the chromatic contrast of the background elements may be reduced. At low levels of visual emphasis, the chromatic contrast may be increased until, by the final level, the chromatic contrast is set at a naturalistic level.

Structure: Units in the visual cortex respond most robustly to stimuli presented against plain, artificially unstructured backgrounds. In contrast, stimuli presented against "natural scene" backgrounds generally result in relatively attenuated responses. To create a very salient stimulus that may drive strong visual cortical responses, an unstructured background may be superior. Thus, at the high levels of visual emphasis, the background may be quite plain, i.e., with few structured distracting elements. At low levels of visual emphasis, the background may become more complex, where at the final level of visual emphasis, the background may be a visually rich, complex background environment.

Object-Background Relation

The following visual aspects or attributes relate to the visual relationship between foreground object(s) and background of a scene, and may be set, adjusted, or modified to achieve a specified visual emphasis.

Luminance contrast between object and background: An impaired visual processor may respond most robustly to an object stimulus that is quite distinct from its background, e.g., along the most basic visual dimensions. A fundamental or primary visual dimension is the light intensity or luminance dimension. Scenes with high degrees of visual emphasis may thus involve objects that differ in luminance from their backgrounds. At low levels of emphasis, more typical luminance contrasts for the object(s) and background may be used.

Chromatic contrast between object and background: Another fundamental visual dimension is the chromatic, i.e., color or hue contrast dimension. High degrees of visual emphasis may involve scenes that contain objects that differ in chromaticity (hue or color) from their backgrounds. Low levels of emphasis may involve more typical chromatic contrasts between the objects and their backgrounds.

Motion/dynamic contrast between object and background: One of the most dramatic methods for creating a salient contrast between an object and its background is to effect relative motion or other dynamic contrast (e.g., flashing or flickering) between the object and its background. High degrees of visual emphasis may involve objects that move in a different direction or at a different velocity from background elements, or that flash or flicker with respect to the background, among other dynamic contrast effects. At low levels of emphasis, the objects may be slow moving or static, or may flash or flicker slightly or slowly, among other dynamic contrast effects.

Texture contrast between object and background: Regular patterns may be an important cue to object segregation. When these patterns are consistent and continuous with the background, the effect is known as camouflage. In this camouflaged state, an impaired visual processor may be challenged to represent an object in a salient fashion. Thus, high visual emphasis may be achieved by utilizing a great deal of texture contrast between the object and its background. Similarly, low visual emphasis may be achieved by utilizing a lesser texture contrast between the object and its background.

Object/background opacity: Opacity refers to the degree to which an object or image is opaque or non-transparent. Thus, at high levels of visual emphasis, the object may be presented on or in a (graphical) layer entirely above the background, resulting in a very sharp, high-contrast border between object and background, thus driving strong responses even in an impaired visual processor. At lower levels of emphasis, the object may be given some transparency or presented in a partially occluded fashion behind background elements.

Object size: An object (e.g., a foreground object) in a scene may be made more noticeable or obvious by increasing the size of the object, e.g., with respect to the background, elements in the background, or the visual field. Thus, at high levels of visual emphasis, the object may be larger, while at low levels of visual emphasis, the object may be smaller. Note that in some embodiments, in addition to, or instead of, such size modification of the foreground object(s) in a scene, the background may be modified by decreasing the size of features in the background. In other words, the background, or features of the background, may be shrunk (or magnified), thereby increasing (or decreasing) the relative size of the foreground object(s) with respect to the background (features). Thus, for example, in an abstract scene where a square (foreground object) is displayed in a background of many circular dots, the dots may be reduced or magnified in size to change the relative size of the square. Either technique may serve to emphasize or enhance the distinction between the object and the background.

Cognitive Training Exercise with Visual Emphasis

Below are described various embodiments of a cognitive training exercise that utilizes visual emphasis to improve cognition, specifically, to improve visual processing in a participant, e.g., an aging adult. More specifically, embodiments of an exercise are presented to improve the ability of the participant to process visual information in a scene presented by a computing device. Said another way, embodiments of the computer-based exercise described herein may operate to renormalize and improve the ability of the visual nervous system of a participant to perceive and process elements in a visual scene.

In one exemplary embodiment, the exercise may include a specified number of stages of emphasis (e.g., 5), beginning initially with the highest degree of visual emphasis and ending at a naturalistic and un-emphasized visual stimulus arrangement. This approach may strongly engage positive plasticity to reorganize information processing in the visual/cognitive systems of individuals with initially poor visual processors. Additionally, embodiments of this visual emphasis approach may move an otherwise very challenging task into a performance range accessible by a person with an impaired visual processor in order to allow them to engage with the task and benefit from the training.

It should be noted that various embodiments of the tasks described herein, or other visual stimulus tasks, may be used singly or in combination in the exercise. Moreover, as described below, in some embodiments, stimulus threshold assessments may also be performed in conjunction with, or as part of, the exercise, thus facilitating more effective training of the participant's visual processing system.

Figure 3:
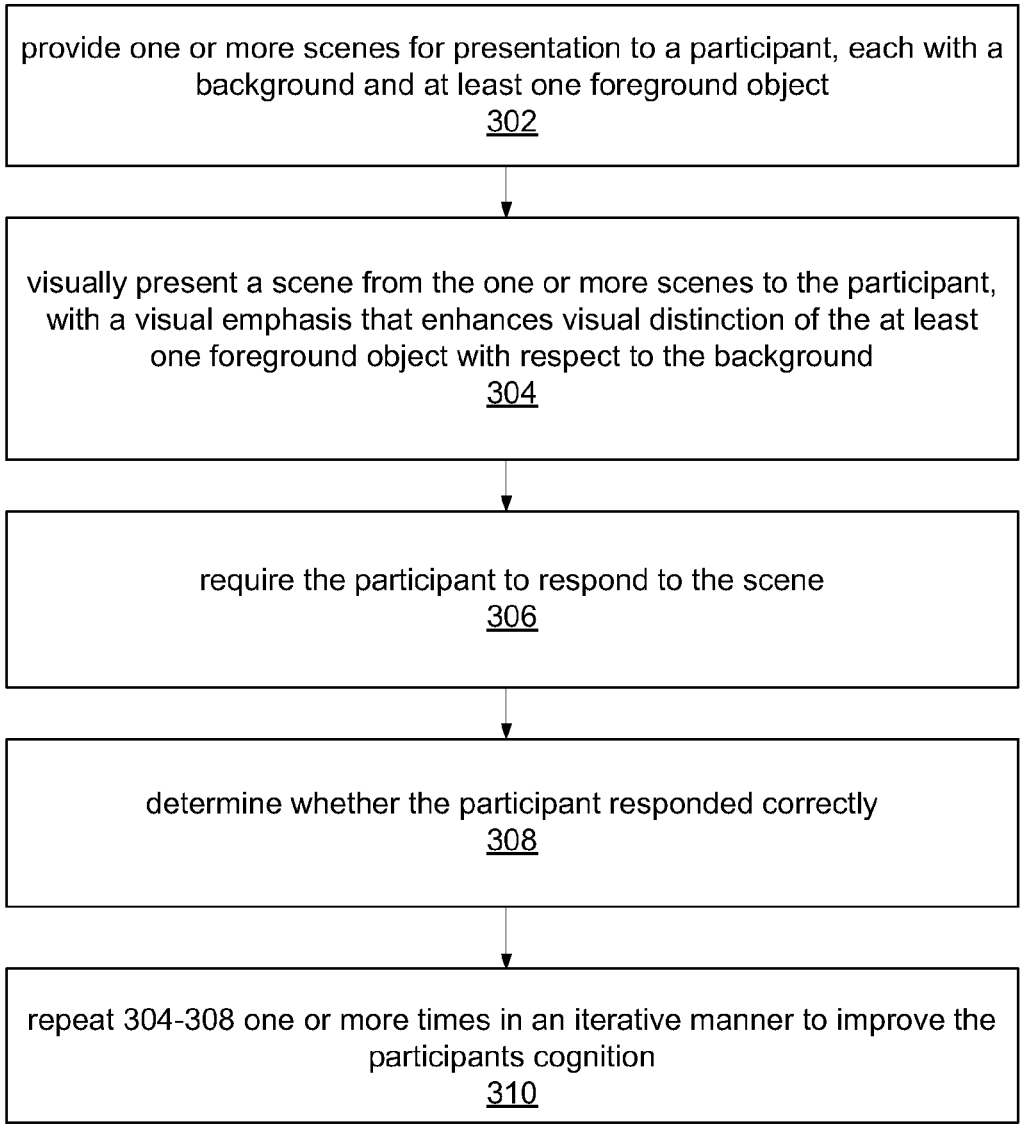
FIG. 3 is a high-level flowchart of one embodiment of a method for cognitive training using visual emphasis, according to one embodiment.

FIG. 3—Flowchart of a Method for Cognitive Training Using Visual Emphasis

FIG. 3 is a high-level flowchart of one embodiment of a method for cognitive training using visual emphasis. More specifically, the method utilizes a computing device to present a scene, including at least one foreground object and a background, where the at least one foreground object and/or the background has been modified to visually emphasize the foreground object(s) with respect to the background, and to record responses from the participant. The method may be used in the context of any of a variety of cognitive training exercises using visual stimuli. It should be noted that in various embodiments, some of the method elements may be performed concurrently, in a different order than shown, or may be omitted. Additional method elements may also be performed as desired. As shown, the method may be performed as follows:

In 302, one or more scenes, each having a background and at least one foreground object, may be provided, where the one or more scenes are available for visual presentation to the participant. For example, the scenes may be stored on a memory medium of the computing device, on a memory medium coupled to the computing device, e.g., over a network, etc. The scenes may be stored as complete scenes, or in separate parts, in separate parts, e.g., backgrounds and foreground objects, and assembled as needed, e.g., for visual presentation to the participant, described below. Note that the backgrounds and foreground objects may be of any type desired, i.e., may have a wide range of complexity, subject matter, and so forth. For example, in some scenes, the background may be a blank visual field, while in others the background may be visually rich in detail, color, etc. Similarly, the at least one foreground object may be singular, or may include a plurality of foreground objects, of any level of complexity desired. For example, foreground objects included in the scenes may include simple objects, e.g., geometrical objects, such as circles, squares, etc., of various colors, sizes, and so forth, or more complex objects, such as images of people, faces, animals, plants, products, machines, buildings, or other structures, among others. In other words, the scenes may include images of any type desired.

In 304, a scene from the one or more scenes may be visually presented to the participant with a specified visual emphasis that visually distinguishes the at least one foreground object with respect to the background. Said another way, visually presenting the scene may include visually presenting the at least one foreground object and/or the background with a specified visual emphasis that visually distinguishes the foreground object(s) with respect to the background. This visual emphasis may facilitate easier perception by the participant of the foreground object(s) against the background.

In some embodiments, this visually presenting with visual emphasis may include modifying the visual emphasis of the at least one foreground object and/or the background to achieve the specified visual emphasis. In other words, the at least one foreground object and/or the background may be graphically processed, such as described above in detail, to emphasize or enhance visual distinction between the foreground object(s) and the background. Thus, for example, some standard image (i.e., foreground object(s) and/or background) may be manipulated or processed "on demand" to achieve the specified visual emphasis.

In other embodiments, the visually presenting with visual emphasis may include selecting the at least one foreground object and/or the background in accordance with the specified visual emphasis to enhance visual distinction of the at least one foreground object with respect to the background. In other words, the at least one foreground object and/or the background may be selected from a set or collection of foreground objects and/or backgrounds that includes foreground objects and/or backgrounds of varying visual emphasis, where the at least one foreground object and/or the background are selected based on the desired or specified degree of visual emphasis. In some embodiments, the set or collection of foreground objects and/or backgrounds may be created by modifying one or more basis or standard foreground objects and/or backgrounds, e.g., according to one or more of the visual emphasis techniques described below, and/or by accumulating or collecting images that happen to include the various levels of visual emphasis.

This distinguishability of foreground object(s) with respect to the background of a scene may be referred to as the salience of the foreground object(s). Said another way, the visual emphasis techniques described herein may operate to make foreground objects more noticeable or obvious to the participant.

As described above, there are a variety of ways the foreground object(s) and/or the background may be modified to visually emphasize the distinctions between them, e.g., to effect visual emphasis for the scene. For example, in various embodiments, the specified visual emphasis may specify one or more of: luminance contrast of the at least one foreground object and/or the background, chromatic contrast of the at least one foreground object and/or the background, spatial frequency of the at least one foreground object and/or the background, size of the at least one foreground object and/or features in the background, flashing the at least one foreground object, moving the at least one foreground object with respect to the background, texture of the at least one foreground object and/or the background, opacity of the at least one foreground object and/or the background, positioning the at least one foreground object with respect to one or more other foreground objects and/or with respect to one or more features of the background, and/or attentional effects of one or more distracting features of the background, among others. In other words, any of the above effects, including any combination of them, may be increased (or decreased) to achieve a specified visual emphasis for the scene.

Figure 4B:
FIGS. 4A and 4B respectively illustrate a standard scene, and an scene with enhanced luminance contrast, according to one embodiment.
Figure 4A:

FIGS. 4A/4B, 5A/5B, 6A/6B, 7A/7B, 8A/8B, and 9A/9B respectively illustrate pairs ("A" and "B" figures) of exemplary screenshots demonstrating specific ways of modifying a scene for visual emphasis, where the first figure of each pair (the "A" figure) presents the scene with no modification, and the second figure of each pair (the "B" figure) illustrates the same scene, but with modification for visual emphasis. As may be seen, in FIG. 4A (and each of the other "A" figures), a foreground object 402, specifically, a duck, is displayed against a background 404, in this case, a lake with surrounding trees, where neither the foreground object 402 nor the background has been modified. Note that the duck is somewhat difficult to perceive against the complex background of the scene. Note further that the scene shown in these figures is meant to be exemplary only, and that any other scenes may be used as desired. Since each of the "A" figures is the same, only the "B" figures are described in detail below, the multiple "A" figures only being included for easy comparison with the "B" figures. Moreover, note that the following figures illustrate only a subset of the various visual emphasis techniques described above.

FIGS. 4A and 4B are exemplary screenshots of above-described scene, where FIG. 4A shows the scene with no visual emphasis, and FIG. 4B shows the scene with modified luminance contrast, specifically, a modified foreground object 403 (duck) and a modified background 405 (wooded lake), where the foreground object 403 is a version of the foreground object 402 of FIG. 4A, but with increased luminance contrast. Note the darker edges and brighter interior of the image of the duck 402. Similarly, the background 405 is a version of the background of FIG. 4A, but with decreased luminance contrast. Note the relative lack of luminance contrast in the background of FIG. 4B. Thus, the luminance contrast of the foreground object has been enhanced, and that of the background diminished, thereby increasing the visibility of the foreground object 403 with respect to the background 405. Note that were the visual emphasis, i.e., the distinguishability of the foreground object with respect to the background, to be decreased instead, the luminance contrast of the foreground object would be decreased, and/or that of the background increased.

FIGS. 5A and 5B are exemplary screenshots of the scene of FIGS. 4A and 4B, but where FIG. 5A shows the scene with no visual emphasis Oust like FIG. 4A), and FIG. 5B shows the scene with modified chromatic or color contrast, specifically, with a modified foreground object 503 and a modified background 505, where, in this example, the foreground object 503 is a version of the foreground object 402 of FIG. 5A (and FIG. 4A), but with increased chromatic contrast. Note the increased color saturation of the duck's head and breast in FIG. 5B as compared to FIG. 5A.

Similarly, the background 505 is a version of the background of FIG. 5A (and FIG. 4A), but with decreased chromatic or color contrast. Note the relative lack of chromatic or color contrast of the background of FIG. 5B as compared to FIG. 5A. Thus, the chromatic (color) contrast of the foreground object has been enhanced, and that of the background diminished, thereby increasing the visibility of the foreground object 503 with respect to the background 505. As with the above modifications, were the distinguishability of the foreground object with respect to the background to be decreased instead, the chromatic or color contrast of the foreground object would be decreased, and/or that of the background increased.

FIGS. 6A and 6B are exemplary screenshots of the scene, where, as with each of the other "A" figures, FIG. 6A shows the scene with no visual emphasis, and FIG. 6B shows the scene with modified spatial frequency, specifically, where the foreground object 603 is a version of the foreground object 402 of FIG. 6A, but with increased spatial frequency. Note the increased sharpness of the duck in FIG. 6B as compared to FIG. 6A. Similarly, the background 605 is a version of the background of FIG. 6A (and each of the other "A" figures), but with decreased spatial frequency. In other words, the background has been filtered to reduce high spatial frequency components—note the relative blurring of the background of FIG. 6B as compared to FIG. 6A. Thus, the spatial frequency of the foreground object has been enhanced, and that of the background diminished, thereby increasing the visibility of the foreground object 603 with respect to the background 605. Of course, as above, were the visual emphasis or distinguishability of the foreground object with respect to the background to be decreased instead, the spatial frequency of the foreground object would be decreased, and/or that of the background increased.

FIGS. 7A and 7B are exemplary screenshots of the scene, where, as with each of the other "A" figures, FIG. 7A shows the scene with no visual emphasis, and FIG. 7B shows the scene, but where the foreground object 703 (the duck) is larger, i.e., has increased size, as compared to FIG. 7A. Thus, the size of the foreground object has been increased, thereby increasing the visibility of the foreground object 703 with respect to the background 705. Of course, making the foreground object 703 smaller would decrease its distinguishability with respect to the background 705, i.e., would decrease the visual emphasis of the scene.

FIGS. 8A and 8B are exemplary screenshots of the scene, where, as with each of the other "A" figures, FIG. 8A shows the scene with no visual emphasis, and FIG. 8B shows the scene, but where the foreground object 803 (the duck) is flashed or flickered, e.g., at some specified frequency, as compared to FIG. 8A. In other words, the foreground object is shown, then removed from view, shown again, removed, and so on in an iterative manner at some frequency, thereby calling the participant's attention to the object. Note that while such flashing cannot be shown in a static image such as FIG. 8B, the reader may imagine the duck 803 flashing, flickering, or blinking on and off. Such flashing of foreground objects may increase the ease with which the participant notices or perceives the foreground objects.

Figures 9A, 9B:
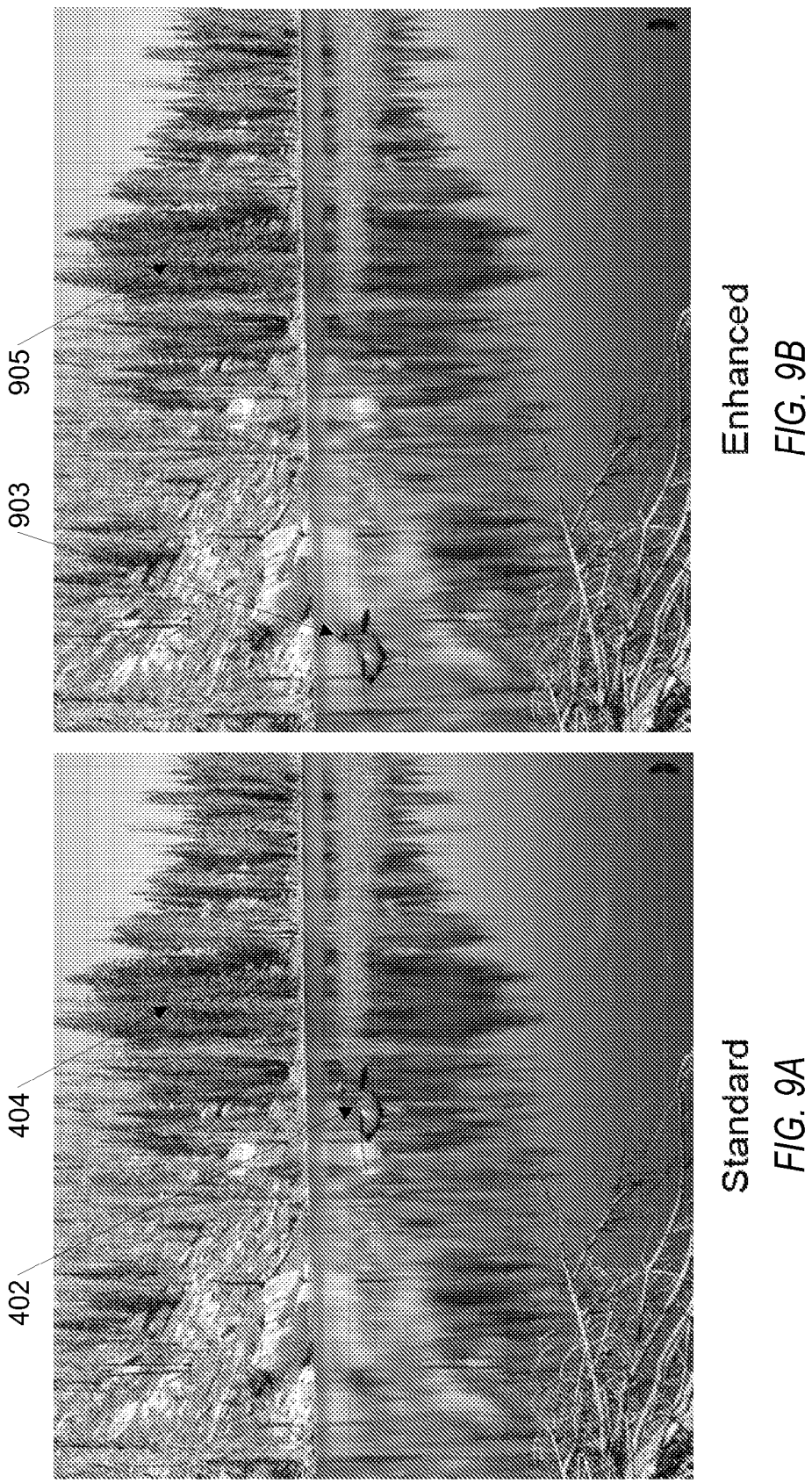
FIGS. 9A and 9B respectively illustrate a standard scene, and an scene with a target in motion, according to one embodiment.

As noted above, in some embodiments, visual emphasis may include moving the at least one foreground object with respect to the background to emphasize or enhance the distinction between them. FIGS. 9A and 9B are exemplary screenshots of the scene, where, as with each of the other "A" figures, FIG. 9A shows the scene with no visual emphasis, and FIG. 9B shows the scene, but where the foreground object 903 (the duck) is moved, e.g., at some specified speed, across the background, as compared to the static foreground object of FIG. 9A. In other words, the foreground object is incrementally moved at some speed with respect to the background, thereby calling the participant's attention to the object. Note that while such movement cannot be shown in a static image such as FIG. 9B, the reader may imagine the duck 903 in motion across the scene. As with the above flashing, such movement of foreground objects may increase the ease with which the participant notices or perceives the foreground objects.

Of course, other means of enhancing visual emphasis or distinction of the foreground object(s) with respect to the background of a scene may be used as desired. As another example, visual emphasis may include positioning the at least one foreground object with respect to one or more other foreground objects and/or with respect to one or more features of the background. In other words, foreground objects and/or background features may be positioned in such a way as to make the foreground object(s) more noticeable. For example, in the duck/lake scene described herein, the duck may be displayed against the blue sky (upper right corner of the image) to increase its salience, or against the trees to decrease its salience. As another example, some of the background features, such as trees, could be moved or positioned to make a clearing surrounding the duck, thereby increasing its noticeability or salience. As a further example, in some embodiments, visual emphasis may include reducing attentional effects of one or more distracting features of the background. For example, if there are features or objects in the background that are confusable with the foreground object(s), these features or objects may be modified to decrease the confusability, e.g., by removing or replacing the features or objects from the scene, changing their coloration, or otherwise making them less noticeable to the participant. As one example, in a scene where a duck is displayed against a background that includes many other, different, birds, the background birds may be replaced with some other animals, e.g., squirrels. Note that the above techniques are meant to be exemplary only, and that other approaches for visual emphasis may be used as desired.

Note further that in some embodiments, two or more the above-described modifications, among others, may be made in conjunction. In other words, in various embodiments, any of the various visual emphasis techniques may be used singly or in combination to enhance or emphasize visual distinction of the foreground object(s) with respect to the background.

In 306, the participant may be required to respond to the scene. For example, in various embodiments, the participant may be required to respond based on information gleaned from foreground objects in the scene, and/or features in the background, e.g., depending on the particular cognitive exercise being performed. In various embodiments, the participant may respond to the scene in any of a variety of ways, including, for example, clicking on objects in the scene with a mouse, clicking on icons or buttons in a graphical user interface (GUI) (possibly within which the scene is displayed), clicking on specified regions in the visual field, pressing keys on a keyboard coupled to the computing device, using voice recognition to enter responses, responding via a touch screen, e.g., by touching objects in the scene, buttons in the GUI, etc., among others. Of course, the particular response required of the participant may depend upon the specific cognitive training being performed, e.g., may depend on the specific cognitive training exercise being performed. Note that in various embodiments, any means for responding to the scene may be used as desired, the above being exemplary only.

In 308, a determination may be made as to whether the participant responded correctly. The response, and/or the correctness/incorrectness of the response, may be recorded. In some embodiments, an indication, e.g., a graphical and/or audible indication, may be provided to the participant indicating the correctness or incorrectness of the participant's response, e.g., a "ding" or a "thunk" may be played to indicate correctness or incorrectness, respectively, and/or points may be awarded (in the case of a correct response). Of course, any other type of indication may be used as desired, e.g., graphical images, animation, etc.

The above visually presenting, requiring, determining, may compose a trial in the exercise or task.

In 310, the visually presenting, requiring, and determining may be repeated one or more times in an iterative manner to improve the participant's cognition and visual processing skills. In other words, a plurality of trials may be performed as described above, preferably using a plurality of different scenes, although multiple trials may certainly be directed to a scene as desired. In some embodiments, multiple trials may be performed under each of a plurality of conditions, e.g., using different types of scenes, with scenes visually presented with different visual emphasis, for different durations, and so forth.

In some embodiments, the specified visual emphasis may be modified based on the determining, e.g., based on whether or not the participant responded correctly a specified number of times (e.g., 1, 10, 40, etc.). Similar to above, modifying the specified visual emphasis may include one or more of: modifying the visual emphasis of the at least one foreground object and/or the background to modify the visual emphasis, and/or selecting a different at least one foreground object and/or a different background for the scene to modify the visual emphasis.

Thus, the repeating of 310 may include adjusting or modifying the (amount or degree of) visual emphasis based on the determining. In some embodiments, for any given visual emphasis technique described herein, the amount of the modification may be adjusted based on the participant's performance. Thus, for example, using the size modification of a foreground object as an example, if the participant responds correctly for some specified number of trials, the size of the foreground object may be decreased for the next trial. Conversely, in one embodiment, if the participant responds incorrectly some specified number of trials, then the size of the foreground object may be increased. Thus, modifying the visual emphasis may include adjusting the degree of visual emphasis based on any of the above visual emphasis techniques, e.g., increasing or decreasing the amount of any particular technique(s).

More generally, modifying the specified visual emphasis may include adjusting the degree of visual emphasis (of the scene) according to one or more visual emphasis techniques. As noted above, visual emphasis is directed to distinguishability of foreground objects against backgrounds, and so there are a number of ways the visual emphasis of a scene may be modified, given access to one or more visual emphasis techniques. As discussed above, each of the one or more visual emphasis techniques specifies a corresponding attribute (e.g., spatial frequency, luminosity contrast, chromatic contrast, etc, described above).

In situations where adjusting the degree of visual emphasis includes increasing the visual emphasis of the scene, increasing the visual emphasis of the scene may be accomplished in any of a variety of ways. For example, in one embodiment, visual emphasis may be increased by increasing the attribute for the at least one foreground object according to a first visual emphasis technique, e.g., sharpening the foreground object(s) by increasing the spatial frequency of the foreground object(s). As another example, visual emphasis may be increased by decreasing the attribute for the background according to a first visual emphasis technique, e.g., blurring the background by decreasing the spatial frequency of the background. As another example, visual emphasis may be increased by increasing the attribute for the at least one foreground object according to a first visual emphasis technique, e.g., sharpening the foreground object(s) by increasing the spatial frequency, and decreasing the attribute for the background according to the first visual emphasis technique, e.g., blurring the background by decreasing the spatial frequency of the background. As yet another example, visual emphasis may be increased by increasing the attribute for at least one foreground object according to a first visual emphasis technique, e.g., sharpening the foreground object(s) by increasing spatial frequency, and decreasing the attribute for the background according to a second visual emphasis technique, e.g., darkening the background by decreasing luminosity, thereby increasing the luminosity contrast between the foreground object(s) and the background.

Conversely, in situations where adjusting the degree of visual emphasis includes decreasing the visual emphasis of the scene, decreasing the visual emphasis of the scene may be accomplished various ways. For example, in one embodiment, visual emphasis may be decreased by decreasing the attribute for the at least one foreground object according to a first visual emphasis technique, e.g., blurring the foreground object(s) by decreasing the spatial frequency of the foreground object(s). As another example, visual emphasis may be decreased by increasing the attribute for the background according to a first visual emphasis technique, e.g., sharpening the background by increasing the spatial frequency of the background. As another example, visual emphasis may be decreased by decreasing the attribute for the at least one foreground object according to a first visual emphasis technique, e.g., blurring the foreground object(s) by decreasing the spatial frequency, and increasing the attribute for the background according to the first visual emphasis technique, e.g., sharpening the background by increasing the spatial frequency of the background. As yet another example, visual emphasis may be decreased by decreasing the attribute for the at least one foreground object according to a first visual emphasis technique, e.g., blurring the foreground object(s) by decreasing spatial frequency, and increasing the attribute for the background according to a second visual emphasis technique, e.g., brightening the background by increasing luminosity, thereby decreasing the luminosity contrast between the foreground object(s) and the background.

Thus, the foreground object(s) and the backgrounds may be modified in various ways using different visual emphasis techniques, possibly in combination, to adjust the visual emphasis of a scene. It should be noted, however, that other combinations of visual emphasis techniques may be used with respect to foreground objects, background objects, or both, as desired.

As noted above, in various embodiments, the various visual emphasis techniques described above may be used singly or in conjunction. Thus, in addition to, or instead of, the above approach to modifying the visual emphasis, in embodiments where the at least one foreground object and/or the background are modified by (or selected in accordance with) one or more of the above visual emphasis techniques, modifying the visual emphasis, e.g., modifying visual aspects of foreground object(s) and/or the background, may include applying or using one or more additional or less of the techniques, based on the participant's response(s), e.g., to make trials easier or more difficult. Thus, for example, if the scene were presented with a specified visual emphasis based on luminance and chromatic contrast, then, based on the participant's response, the number and/or type of visual emphasis techniques applied to the scene may be changed. For example, to make trials easier, the visual emphasis may be increased, e.g., by further applying a spatial frequency emphasis, e.g., increasing the sharpness of the foreground object (in addition to the luminance and chromatic contrast) thereby making the stimulus (the scene) more easily perceived, and conversely, to increase the difficulty of trials, then the visual emphasis may be decreased, e.g., by removing one (or more) of the luminance contrast or chromatic contrast emphasis, thereby making the stimulus (the scene) more difficult to perceive. In other words, decreasing the visual emphasis may include ceasing to perform at least one of the one or more modification techniques, thereby making the next trial more difficult.

Described more specifically, in embodiments where modifying the visual emphasis includes modifying one or more of: luminance contrast of the at least one foreground object and/or the background, color contrast of the at least one foreground object and/or the background, spatial frequency of the at least one foreground object and/or the background, size of the at least one foreground object and/or features in the background, flashing the at least one foreground object, moving the at least one foreground object with respect to the background, texture of the at least one foreground object and/or the background, positioning the at least one foreground object with respect to one or more other foreground objects and/or with respect to one or more features of the background, and/or reducing attentional effects of one or more distracting features of the background, increasing the visual emphasis may include increasing one or more others of the luminance contrast, color contrast, spatial frequency, size, flashing, moving, texture, positioning, or reducing attentional effects, thereby making the next trial less difficult, and decreasing the visual emphasis may include ceasing to modify at least one of the one or more of: luminance contrast, color contrast, spatial frequency, size, flashing, moving, texture, positioning, or reducing attentional effects, thereby increasing the difficulty of trials.

In yet another embodiment, the visual emphasis of the scene may be modified by exchanging or switching out an applied visual emphasis technique, e.g., color or chromatic contrast, with another visual emphasis technique, e.g., movement of the foreground object(s), with the presumption that various of the visual emphasis techniques described herein may differ in the perceptual effects they have with respect to the participant.

Thus, in some embodiments, the number of modification techniques brought to bear on the scene may change based on whether the visual emphasis is to be increased or decreased.

In preferred embodiments, the visual emphasis of the scene may be determined by the stage of training that a participant is in, which itself may be based on the number of trials the participant has performed correctly. For example, at the beginning of a training program, scenes may be presented with a high level of visual emphasis, i.e., with a specified high degree of one or more of the visual emphasis aspects or attributes described above (e.g., luminance or chromatic contrast, spatial frequency, size, etc.), to engage the participant, and to facilitate easier perception of foreground objects against backgrounds. As the participant progresses, the scenes may be presented with lower levels of visual emphasis.

For example, the degree of visual emphasis may be determined by the participant's cumulative success or progress in the exercise, e.g., beginning with high visual emphasis scenes, when the participant has responded correctly some specified number of times, i.e., has correctly performed the specified number of trials, the specified visual emphasis may be decreased. Each time the participant has correctly responded the specified number of times (or a different specified number of times), the specified visual emphasis may be decreased again, and so forth, until the scenes are substantially un-emphasized, or even de-emphasized. In other words, the repeating may include beginning with scenes of higher visual emphasis, and the method may further include decreasing the visual emphasis if the participant responds correctly a specified number of times, i.e., the visual emphasis levels may be changed (decreased) after a specified number of correct responses.

Thus, as the participant correctly performs increasing numbers of trials, the visual emphasis of the presented scenes may decrease. There may be a specified number of levels (e.g., 5), where the participant progresses through the levels from highest emphasis to lowest emphasis. In other words, the participant may progress through a plurality of levels, with each successive level specifying lower visual emphasis.

FIGS. 10-14 illustrate exemplary scenes at different levels of visual emphasis, specifically, at 5 different visual emphasis levels, although it should be noted that other numbers of levels may be used as desired.

Figure 10:
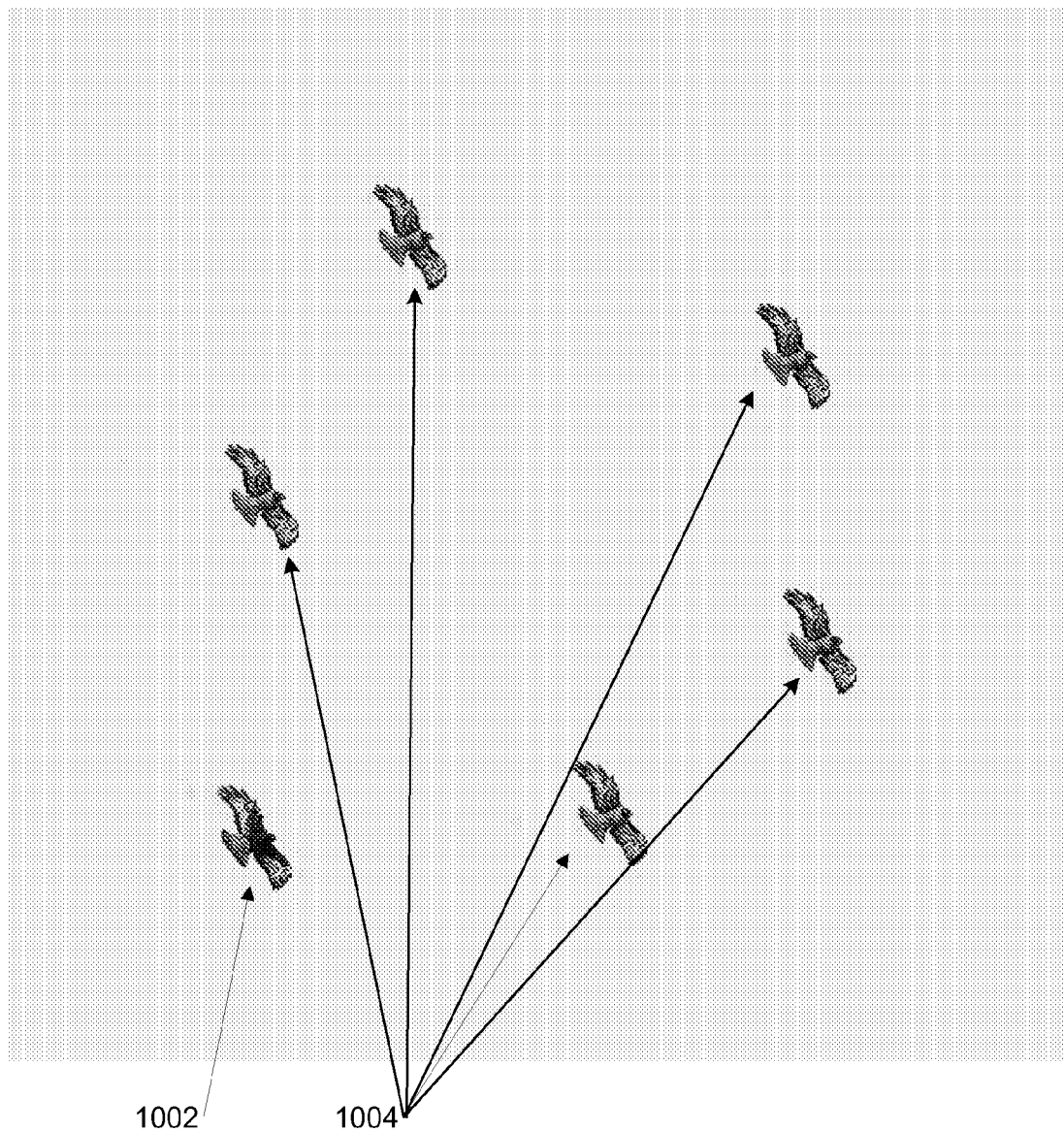
FIGS. 10-14 illustrate exemplary scenes at various visual emphasis levels.

FIG. 10 illustrates an exemplary level 1, high visual emphasis scene, where a target bird 1002 and a plurality of distracter birds 1004 are displayed against a light blue background. In this scene, the birds are sharpened, the color contrast is increased, and the luminance is reduced to create a large contrast from the light background. The unstructured background creates maximal spatial frequency and texture contrast between object and background. The target bird 1002 is the red tail morph hawk in the lower left corner. The other birds are identical illustrations of a red tail hawk. The birds are chosen based on their relative discriminability; however, this choice is not germane to the present discussion of visual emphasis.

Figure 11:
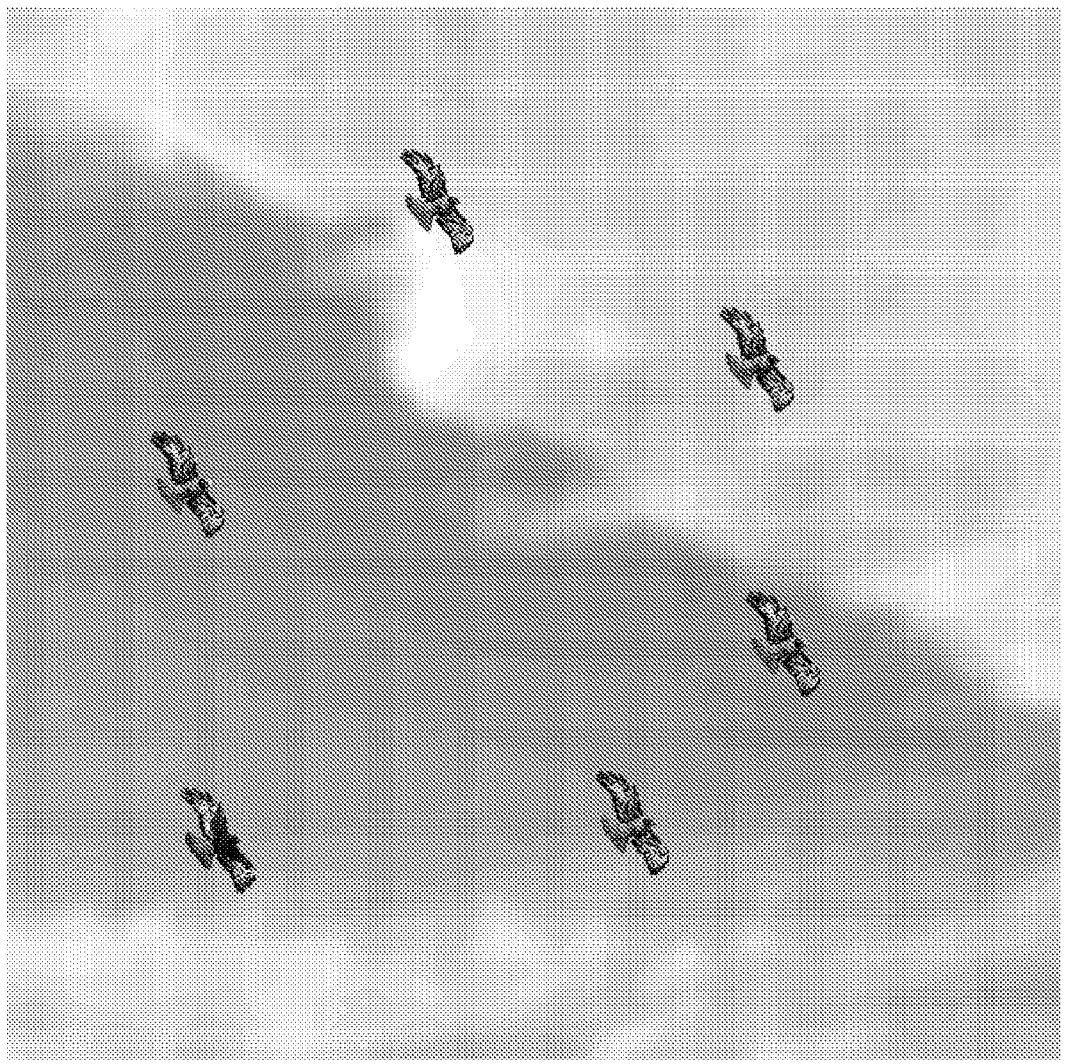

FIG. 11 illustrates an exemplary level 2, medium-high visual emphasis scene. The birds are the same as in the level 1 FIG. 10. However, in this scene, naturalistic background structure has been added, though blurred. The luminance and chromatic contrast of the background has also been modified and the blue parts of the sky are darker to be closer to the luminance of the birds. Thus, the birds are not quite as distinguishable from the background as those in FIG. 10.

Figure 12:

FIG. 12 illustrates and exemplary level 3, medium visual emphasis scene. In this scene, the birds are sharpened, the color contrast is increased, and the luminance is reduced to create a large contrast from the light background, although each of these effects is applied significantly less than in level 1. Additionally, more textural, chromatic, and luminance contrast structure is added to the background, with a slight blurring. Note also that the complexity of the background has been increased. Thus, the birds of FIG. 12 may be somewhat less distinguishable from the background as compared to FIG. 11.

Figure 13:
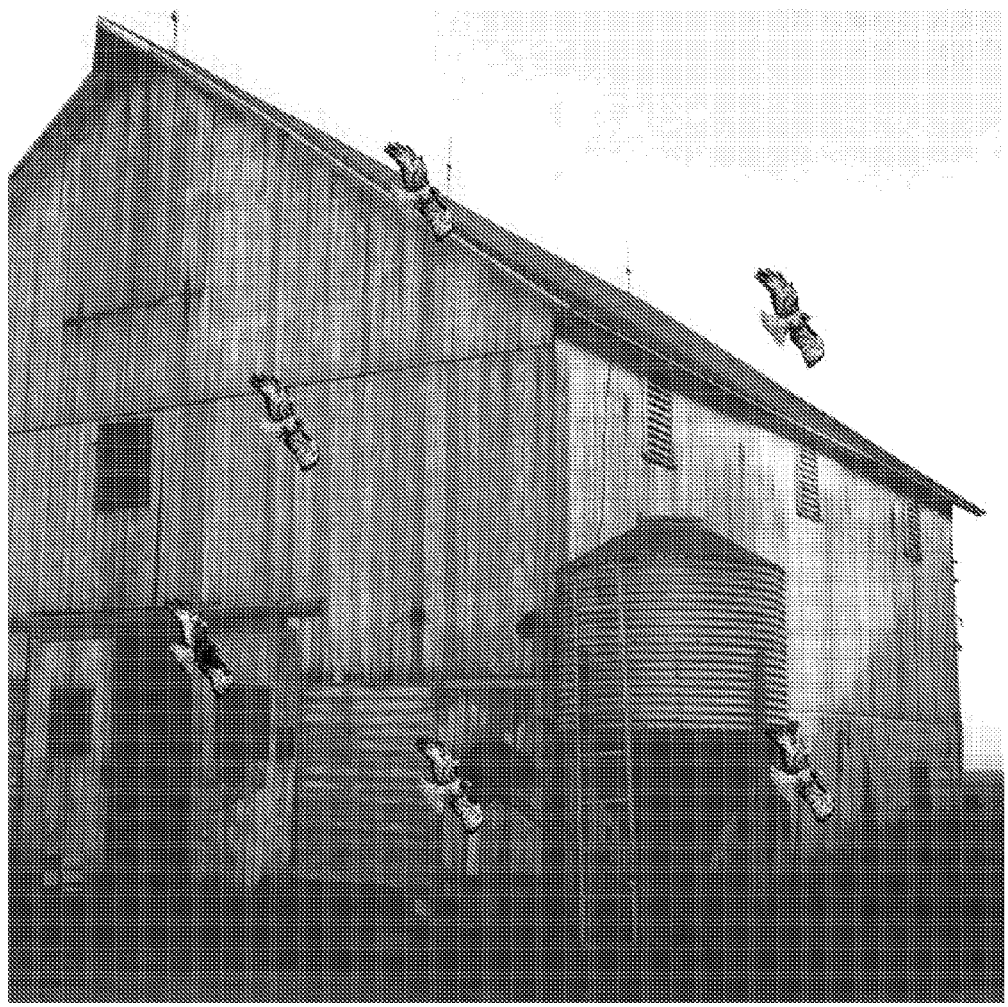

FIG. 13 illustrates an exemplary level 4, low visual emphasis scene. In this case, the birds presented are photo-realistic drawings mimicking the appearance of a canonical bird of each type, where the images are not altered or modified for visual emphasis. The background is based on a photograph of a barn, and is also unaltered. The internal spatial frequency content, color, luminance, color contrast, luminance contrast and texture of the background are quite similar to those of the foreground objects. This example thus represents a case that is close to a natural scene. However, without some blur and/or transparency in the foreground objects, there is an artificially large apparent plane difference (as though they are taken from different scenes), due in part to inconsistent lighting effects.

Figure 14:

FIG. 14 illustrates an exemplary level 5, low visual emphasis scene. In this case, the birds are slightly blurred and some transparency is added to make the birds blend into the background. Also, the chromatic contrast and luminance contrast of the background is manipulated to be more similar to that of the birds. Thus, while the scene still represents a plausible natural scene, scene elements have been modified to decrease the distinguishability of the foreground objects from the background.

Thus, preferred embodiments of the exercise may include specified levels of visual emphasis through which the participant may progress based on successful performance of trials, where the progression proceeds from high visual emphasis levels to low visual emphasis levels.

In other embodiments, the visual emphasis of the scene for the subsequent trial may be modified or adjusted depending on whether the participant responded correctly or incorrectly for the trial. For example, in one embodiment, if the scene were presented with a specified visual emphasis, i.e., with a specified degree of one or more of the visual emphasis aspects or attributes described above (e.g., luminance or chromatic contrast, spatial frequency, size, etc.), then, based on the participant's response, the degree of visual emphasis applied to the scene may be modified or changed. For example, if the participant responded incorrectly, then the visual emphasis may be increased, i.e., one or more of the aspects or attributes described above may be increased, thereby making the stimulus (the scene) more easily perceived, and conversely, if the participant responded correctly, then the visual emphasis may be decreased, i.e., one or more of the aspects or attributes described above may be decreased, thereby making the stimulus (the scene) more difficult to perceive.

In one embodiment, visually presenting the scene may include visually presenting the scene at a specified stimulus intensity. As used herein, the term "stimulus intensity" refers to an adaptable or adjustable attribute of the scene or its presentation that may be modified or adjusted to make trials more or less difficult. The above-described adjusting of the visual emphasis may compose (or include, or result in) adjusting the stimulus intensity. In other words, by adjusting the visual emphasis, the stimulus intensity of the scene may be adjusted or modified. Said another way, in some embodiments, the stimulus intensity may be or include the visual emphasis. In preferred embodiments, adjusting the stimulus intensity may be performed using a maximum likelihood procedure, such as, for example, a QUEST (quick estimation by sequential testing) threshold procedure, and/or a ZEST (zippy estimation by sequential testing) threshold procedure, described below, whereby threshold values for the stimulus intensity may be determined based on the participant's performance.

In some embodiments, adjusting the stimulus intensity may include adjusting the stimulus intensity (e.g., the visual emphasis) to approach and substantially maintain a specified success rate for the participant, e.g., using a single stair maximum likelihood procedure, also described below. Moreover, the repeating may include assessing the participant's performance a plurality of times during the repeating. In other words, not only may the stimulus intensity (e.g., the amount of modification) be adjusted on a per trial basis based on the participant's performance, but the participant's performance may be assessed periodically during the exercise, e.g., before, one or more times during, and after the exercise. A description of threshold determination/assessment is provided below. In some embodiments, assessing the participant's performance a plurality of times may be performed according to the maximum likelihood procedure (e.g., QUEST or ZEST). Additionally, in some embodiments, the assessing the participant's performance a plurality of times may be performed using a 2-stair maximum likelihood procedure, described below. Thus, as described below, the repeating may include performing threshold assessments in conjunction with, or as part of, the exercise.

Threshold Determination/Assessment

As indicated above, stimulus intensity is an adjustable attribute of a presented stimulus, e.g., a scene, whereby the task or a trial in the task may be made more or less difficult. For example, as noted above, the stimulus intensity may refer to the amount or degree that the scene, or one or more elements in the scene, is modified in accordance with one or more of the above-described techniques, i.e., the degree of visual emphasis used in the scene, although it should be noted that any other attribute or combination of attributes may be used as desired, the term stimulus intensity being intended to refer to any such adjustable attributes.

A stimulus intensity threshold is the value of the stimulus intensity at which the participant achieves a specified level of success, e.g., 0.9, corresponding to a 90% success rate. Exercise based assessments (i.e., threshold determination) are designed to assess a participant's threshold with respect to stimuli on a given exercise, and can be used to adjust stimulus presentation to (substantially) achieve and maintain a desired success rate for the participant, e.g., with respect to a particular exercise, task, and/or condition. As will be described below, such threshold determination may also be used to assess or determine a pre-training threshold that can then be used to calibrate the program to an individual's capabilities on various exercises, as well as serve as a baseline measure for assessing the participant's performance periodically during an exercise. Such assessment may also serve as a baseline measure to which post-training thresholds can be compared. Comparison of pre-training to post-training thresholds may be used to determine the gains made as a function of training with the cognition enhancement exercise or tasks described herein.

As noted above, there are various approaches whereby such thresholds may be assessed or determined, such as, for example, the well known QUEST (Quick Estimation by Sequential Testing) threshold method, which is an adaptive psychometric procedure for use in psychophysical experiments, or a related method, referred to as the ZEST (Zippy Estimation by Sequential Testing) procedure or method, among others, although it should be noted that such methods have not heretofore been utilized in cognition enhancement training exercises using visual stimuli, as described herein.

The ZEST procedure is a maximum-likelihood strategy to estimate a subject's threshold in a psychophysical experiment based on a psychometric function that describes the probability a stimulus is detected as a function of the stimulus intensity. For example, consider a cumulative Gaussian psychometric function, $F(x-T)$, for a 4-alternative-forced-choice (afc) task with a 5% lapsing rate, with proportion correct (ranging from 0-1) plotted against intensity of the stimulus (ranging from 0-5). As used herein, the term intensity (with respect to stimuli) refers to the value of the adaptive dimension variable being presented to the participant at any particular trial in a particular exercise. In other words, the intensity value is that parameter regarding the exercise stimuli that may be adjusted or adapted, e.g., to make a trial more or less difficult. For example, in preferred embodiments of the cognitive training exercise described herein, the intensity value is the degree to which a scene, or elements in a scene, is visually emphasized, i.e., the visual emphasis. The threshold is defined to be the mean of the Gaussian distribution for a specified success rate—e.g., a value yielding some specified success rate, e.g., 60%, 90%, etc.

The method may make some assumptions about the psychophysics:

1. The psychometric function has the same shape, except a shift along the stimulus intensity axis to indicate different threshold value.
2. The threshold value does not change from trial to trial.
3. Individual trials are statistically independent.

The primary idea of the ZEST procedure is as follows: given a prior probability density function (P.D.F.) centered around the best threshold guess, x, this P.D.F. is adjusted after each trial by one of two likelihood functions, which are the probability functions that the subject will respond "yes" or "no" to the stimulus at intensity as a function of threshold. Since the psychometric function has a constant shape and is of the form $F(x-T)$, fixing the intensity x and treating threshold T as the independent variable, the "yes" likelihood, $p=F(-$ (T−x)), is thus the mirror image of the psychometric function about the threshold, and the "no" likelihood function is then simply 1−p.

The P.D.F. is updated using Bayes' rule, where the posterior P.D.F. is obtained by multiplying the prior P.D.F. by the likelihood function corresponding to the subject's response to the trial's stimulus intensity. The mean of the updated (or posterior) P.D.F. is then used as the new threshold estimate and the test is repeated with the new estimate until the posterior P.D.F. satisfies a confidence interval criteria (e.g. standard deviation of posterior P.D.F.<predetermined value) or a maximum number of trials is reached.

In one example of the ZEST procedure, a single trial of a 4-afc experiment is performed, with x=2.5 (intensity) as the initial threshold guess. If the subject responds correctly, the next trial is placed at the mean of the corresponding posterior P.D.F., ~x=2.3; if the response is incorrect, the next trial is placed at the mean of the corresponding P.D.F., ~x=2.65. This sequential adjustment of stimulus intensity is referred to as a single stair maximum likelihood procedure because the value of the stimulus intensity is raised or lowered (based on the participant's performance) along a single "track", i.e., only one series of values of the intensity is managed.

Thus, in some embodiments, a single stair ZEST procedure such as that described above may be used to adjust the intensity of the stimuli for the trials during training. In contrast, in some embodiments, particularly with respect to the periodic assessments during the exercise (as opposed to the "per response" stimulus adjustment) a 2-stair ZEST procedure may be employed, where two independent tracks with starting values, preferably encompassing the true threshold, each running its own ZEST procedure, are randomly interleaved in the threshold seeking procedure. In addition to their individual termination criterion, the difference between the two stairs may also be required to be within a specified range, e.g., the two stairs may be constrained to be a predetermined distance apart. An exemplary implementation of this approach is described below with respect to visual emphasis threshold assessment.

As used herein, the parameters required for ZEST may include the mean of the prior P.D.F. (threshold estimate), the standard deviation of the prior P.D.F. (spread of threshold distribution), the standard deviation of the cumulative Gaussian distribution (slope of psychometric function), the maximum number of trials to run, and a confidence level and interval. Additionally, in one embodiment, the trial-by-trial data saved for analysis may include: the track used, the stimulus intensity presented, the subject's response, the mean of posterior P.D.F., and the standard deviation of the posterior P.D.F., as well as any other data deemed necessary or useful in determining and/or assessing the participant's threshold.

Thus, in preferred embodiments, a maximum likelihood procedure, such as a ZEST procedure, may be used to adjust the stimulus intensity for trials during training (e.g., via a single stair ZEST procedure, possibly per condition), and may also be used for assessment purposes at periodic stages of the exercise (e.g., via a dual stair ZEST procedure, describe below). In one embodiment, such assessment may occur at specified points during the exercise, e.g., at 0% (i.e., prior to beginning), 25%, 50%, 75%, and 100% (i.e., after completion of the exercise) of the exercise. An example of such assessment is now described.

A primary purpose of the exercise threshold assessment is to determine the minimum amount of visual emphasis for a scene in the exercise that a person can respond correctly to above a statistical threshold. The exercise assessment may be similar to the exercise with respect to visual presentation, where the differences between the assessment and the exercise lie (at least primarily) in the movement or progression through the task and the data that are obtained from this movement for the assessment. The procedure is designed to obtain a threshold, which is a statistical rather than an exact quantity. In one embodiment, for the purposes of this exercise, the threshold may be defined as the smallest degree of visual emphasis used in a scene for the exercise at which the participant will respond correctly a specified percentage, e.g., 69%, 90%, etc., of all trials for the task. In a preferred embodiment, being a computer based task, the assessment may use the ZEST procedure to progress or move through the task, adjust the value of the stimulus intensity (i.e., amount of visual emphasis) for the exercise, and determine the statistical threshold.

As noted above, many aspects of the assessment may generally be similar, or possible even identical, to the exercise with respect to visual presentation. However, some aspects of the exercise version may not be necessary in the assessment. For example, with regard to the GUI, in some embodiments, GUI elements such as score indicator, number missed, etc., that may be used in the exercise may not be necessary, and so may be omitted. Features or assets that may remain the same may include such features as the "ding" and "thunk" sounds that play after a participant responds correctly or incorrectly. The assessment stimulus presentation may also be identical to the training version.

The following describes one embodiment of a 2-stair (dual track) approach for determining a psychophysical threshold for a participant, e.g., an aging adult, where, as noted above, the stimulus intensity is the amount of visual emphasis in a scene. Initially, first and second tracks may be initialized with respective values or degrees of visual emphasis based on an initial anticipated threshold, where the initial anticipated threshold is an initial estimate or guess of the visual emphasis corresponding to a specified performance level of the participant, e.g., the amount of visual emphasis at which the participant responds correctly some specified percentage of the time, e.g., 50%. For example, in one embodiment, the first track may be initialized to a first amount of visual emphasis that is below the initial anticipated threshold, e.g., preferably just slightly below the initial anticipated threshold, and the second track may be initialized to a second amount of visual emphasis that is (e.g., slightly) above the initial anticipated threshold. Thus, the initial values of the two tracks may straddle the initial anticipated threshold.

The method elements 302-304 of FIG. 3 may be performed, as described above, where a scene is presented in accordance with the visual emphasis of a specified one of either the first track or the second track. In other words, one of the tracks may be selected or otherwise determined, and the stimuli for the trial may be presented with a visual emphasis specified by the selected track. Thus, in preferred embodiments, the initial anticipated threshold, the first amount of visual emphasis, the second amount of visual emphasis, and the (to be determined) threshold, each is or specifies a respective amount or degree of visual emphasis. As also described above, the participant may be required to respond to the scene (306), and a determination may be made as to whether the participant responded correctly (308).

The visual emphasis of the specified track may then be adjusted or modified, based on the participant's response. For example, the amount of visual emphasis of the track may be modified in accordance with a maximum likelihood procedure, such as QUEST or ZEST, as noted above. In one embodiment, for each track, modifying the amount of visual emphasis of the specified track based on the participant's response may include increasing the amount of visual emphasis if the participant responds incorrectly, and decreasing the amount of visual emphasis if the participant responds correctly. Thus, for each assessment trial (in a given track), the amount of visual emphasis for that trial may be determined by the performance of the previous trial for that track. In other words, the participant's response to the stimulus determines that track's next amount of visual emphasis via the maximum likelihood method.

Similar to 310 of FIG. 3, the visually presenting, requiring, and determining, (and modifying or adjusting of the (amount or degree of) visual emphasis), may be repeated one or more times in an iterative manner, but in this case, the repeating is performed to determine respective final values or amounts of visual emphasis for the first track and the second track. For example, in one embodiment, trials in the first track and the second track may be performed in an alternating manner, or, alternatively, trials may be performed in the first track and the second track randomly with equal probability. Thus, over numerous trials, the number of trials performed in each track should be equal, or at least substantially equal. In preferred embodiments, the presenting, requiring, determining, and modifying, may be repeated until the amounts of visual emphasis of the first track and the second track have converged to values within a specified confidence interval, and where the values are within a specified distance from each other, or, until a specified number of trials have been conducted for each track. In other words, the repetition may continue until either some maximum number of trials has been performed, or until convergence conditions for the tracks have been met, both singly, and together. For example, each track may be required converge to a respective value, and the convergent values for the two tracks may be required to be within some distance or interval of each other.

A threshold for the participant may then be determined based on the respective final amounts of visual emphasis for the first track and the second track, where the threshold is or specifies the amount of visual emphasis of scenes associated with the specified performance level of the participant. For example, as mentioned above, the determined threshold may specify the amount of visual emphasis at which the participant responds correctly some specified percentage of the trials, e.g., 50%, 90%, etc., although it should be noted that any other percentage may be used as desired. In one embodiment, the threshold for the participant may be determined by averaging the respective final numbers of target images for the first track and the second track.

Figure 15:
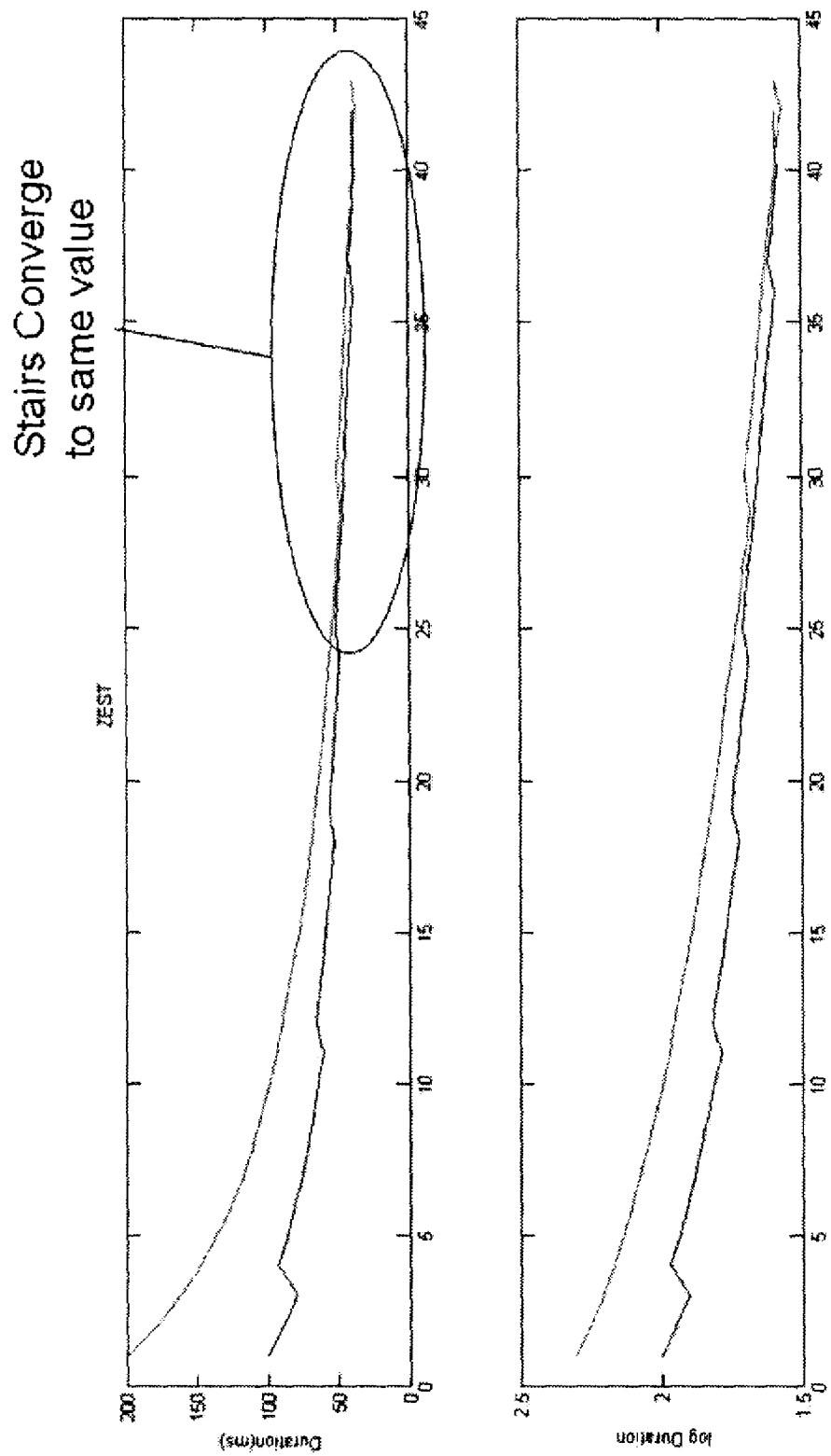
FIG. 15 illustrates convergence to a threshold value over a series of trials in an exemplary two-stair ZEST threshold procedure.

FIG. 15 illustrates an exemplary case where two tracks or "stairs" used in a ZEST threshold procedure are shown converging to a threshold value over a series of trials, where in this case the stimulus intensity is a duration, e.g., the presentation time of a stimulus. Note that in the top graph, duration vs. trials is plotted in a linear manner, whereas the bottom graph provides the same information but is logarithmic on the duration (vertical) axis. As may be seen, after about 25 trials, the two tracks or stairs converge to a value at or near 50 ms, thus, the two tracks, initialized respectively to values above and below an initial estimate of the threshold, converge to an approximation of the participant's actual stimulus threshold for the exercise.

In some embodiments, the presenting, requiring, determining, and modifying may compose performing a trial, and certain information may be saved on a per trial basis. For example, in one embodiment, for each trial, the method may include saving one or more of: which track was used in the trial, the number of target images used in the trial, the number of distracter images presented to the participant in the trial, the participant's selection, the correctness or incorrectness of the participant's response, the mean of a posterior probability distribution function for the maximum likelihood procedure, and the standard deviation of the posterior probability distribution function for the maximum likelihood procedure, among others. Of course, any other data related to the trial may be saved as desired, e.g., the distinguishing attribute of the target image, eccentricity of the target image, and/or any other condition of the tracking task.

Additionally, in some embodiments, various parameters for the maximum likelihood procedure besides the respective (initial) durations of the two tracks may be initialized, such as, for example, the standard deviation of a cumulative Gaussian psychometric function for the maximum likelihood procedure, and/or the standard deviation of a prior threshold distribution for the maximum likelihood procedure.

In one embodiment, the method may include determining the initial anticipated threshold. For example, the initial anticipated threshold may be determined based on one or more of: the age of the participant, calibration trials performed by the participant, and/or calibration trials performed by other participants, e.g., in a "pilot" program, although it should be noted that any other type of information may be used as desired to determine the initial anticipated threshold.

In some embodiments, certain information may be maintained and recorded over the course of the exercise. For example, in one exemplary embodiment, the following information may be recorded: the name of the participant; the age of the participant; the gender of the participant; the number of assessments/training segments completed; all scores achieved during the exercise; all threshold estimates for training and assessments; ZEST progressions used in the exercise; task type, conditions and colors used for each trial, session, or level; screen frame rate and spatial resolution; time/date for each session; time spent on each task; and the number of training trials, sessions, or levels and assessments completed. Of course, this information is meant to be exemplary only, and other information may be recorded as desired.

In some embodiments, the method may also include performing a plurality of practice trials, i.e., prior to performing the method elements described above. For example, in some embodiments, one or more practice sessions may be performed prior to the beginning of training to familiarize the participant with the nature and mechanisms of the task. In each practice session, a specified number of trials (e.g., 5) for each of one or more practice conditions may be performed. In some embodiments, the participant may be able to invoke such practice sessions at will during the exercise, e.g., to re-familiarize the participant with the task at hand.

It should be noted that the particular exercise disclosed herein is meant to be exemplary, and that any other repetition-based cognitive training exercises using visual stimuli with multiple stimulus sets may be used as desired, possibly in combination. In other words, the visual stimulus exercise with visual emphasis described herein is but one example of a cognitive training exercise using a computing system to present visual stimuli to a participant, record the participant's responses, and modify some aspect of the visual stimuli based on these responses, where these method elements are repeated in an iterative manner using multiple sets of stimuli to improve the ability of the participant to process visual information. Note particularly that such cognitive training using a variety of such visual stimulus-based exercises, possibly in a coordinated manner, is contemplated.

Those skilled in the art should appreciate that they can readily use the disclosed conception and specific embodiments as a basis for designing or modifying other structures for carrying out the same purposes of the present invention without departing from the spirit and scope of the invention as defined by the appended claims. For example, various embodiments of the methods disclosed herein may be implemented by program instructions stored on a memory medium, or a plurality of memory media.

The invention claimed is:

1. A method for enhancing cognition in a participant, utilizing a computing device to present visual stimuli for training, and to receive responses from the participant, the method comprising:

utilizing the computing device to perform:
providing one or more scenes, each having a background and at least one foreground object, wherein the one or more scenes are available for visual presentation to the participant;
visually presenting a scene from the one or more scenes to the participant, wherein said visually presenting comprises visually presenting the at least one foreground object and/or the background with a specified visual emphasis that visually distinguishes the at least one foreground object with respect to the background;
requiring the participant to respond to the scene;
determining whether the participant responded correctly;
modifying the specified visual emphasis based on said determining, wherein said modifying the specified visual emphasis comprises adjusting the degree of visual emphasis according to one or more visual emphasis techniques; and
repeating said visually presenting, said requiring, and said determining one or more times in an iterative manner to improve the participant's cognition.

2. The method of claim 1, wherein said visually presenting the at least one foreground object and/or the background with a specified visual emphasis comprises one or more of:
modifying the visual emphasis of the at least one foreground object and/or the background to achieve the specified visual emphasis; or
selecting the at least one foreground object and/or the background in accordance with the specified visual emphasis.

3. The method of claim 1, wherein the specified visual emphasis specifies:
luminance contrast of the at least one foreground object and/or the background.

4. The method of claim 1, wherein the specified visual emphasis specifies:
chromatic contrast of the at least one foreground object and/or the background.

5. The method of claim 1, wherein the specified visual emphasis specifies:
spatial frequency of the at least one foreground object and/or the background.

6. The method of claim 1, wherein the specified visual emphasis specifies:
size of the at least one foreground object and/or features in the background.

7. The method of claim 1, wherein the specified visual emphasis specifies:
flashing the at least one foreground object.

8. The method of claim 1, wherein the specified visual emphasis specifies:
moving the at least one foreground object with respect to the background.

9. The method of claim 1, wherein the specified visual emphasis specifies:
texture of the at least one foreground object and/or the background.

10. The method of claim 1, wherein the specified visual emphasis specifies:
opacity of the at least one foreground object and/or the background.

11. The method of claim 1, wherein the specified visual emphasis specifies:
positioning the at least one foreground object with respect to one or more other foreground objects and/or with respect to one or more features of the background.

12. The method of claim 1, wherein the specified visual emphasis specifies:
attentional effects of one or more distracting features of the background.

13. The method of claim 1, wherein said modifying the specified visual emphasis comprises one or more of:
modifying the visual emphasis of the at least one foreground object and/or the background to modify the visual emphasis; or
selecting a different at least one foreground object and/or a different background for the scene to modify the visual emphasis.

14. The method of claim 1, wherein each of the one or more visual emphasis techniques specifies a corresponding attribute, wherein said adjusting the degree of visual emphasis comprises increasing the visual emphasis of the scene, and wherein said increasing the visual emphasis of the scene comprises:
increasing the attribute for the at least one foreground object according to a first visual emphasis technique.

15. The method of claim 1, wherein each of the one or more visual emphasis techniques specifies a corresponding attribute, wherein said adjusting the degree of visual emphasis comprises increasing the visual emphasis of the scene, and wherein said increasing the visual emphasis of the scene comprises:
decreasing the attribute for the background according to a first visual emphasis technique.

16. The method of claim 1, wherein each of the one or more visual emphasis techniques specifies a corresponding attribute, wherein said adjusting the degree of visual emphasis comprises increasing the visual emphasis of the scene, and wherein said increasing the visual emphasis of the scene comprises:
increasing the attribute for the at least one foreground object according to a first visual emphasis technique; and
decreasing the attribute for the background according to the first visual emphasis technique.

17. The method of claim 1 wherein each of the one or more visual emphasis techniques specifies a corresponding attribute, wherein said adjusting the degree of visual emphasis comprises increasing the visual emphasis of the scene, and wherein said increasing the visual emphasis of the scene comprises:
increasing the attribute for the at least one foreground object according to a first visual emphasis technique; and
decreasing the attribute for the background according to a second visual emphasis technique.

18. The method of claim 1, wherein each of the one or more visual emphasis techniques specifies a corresponding attribute, wherein said adjusting the degree of visual emphasis comprises decreasing the visual emphasis of the scene, and wherein said decreasing the visual emphasis of the scene comprises:

decreasing the attribute for the at least one foreground object according to a first visual emphasis technique.

19. The method of claim 1, wherein each of the one or more visual emphasis techniques specifies a corresponding attribute, wherein said adjusting the degree of visual emphasis comprises decreasing the visual emphasis of the scene, and wherein said decreasing the visual emphasis of the scene comprises:

decreasing the attribute for the background according to a first visual emphasis technique.

20. The method of claim 1, wherein each of the one or more visual emphasis techniques specifies a corresponding attribute, wherein said adjusting the degree of visual emphasis comprises decreasing the visual emphasis of the scene, and wherein said decreasing the visual emphasis of the scene comprises:

decreasing the attribute for the at least one foreground object according to a first visual emphasis technique; and increasing the attribute for the background according to the first visual emphasis technique.

21. The method of claim 1, wherein each of the one or more visual emphasis techniques specifies a corresponding attribute, wherein said adjusting the degree of visual emphasis comprises decreasing the visual emphasis of the scene, and wherein said decreasing the visual emphasis of the scene comprises:

decreasing the attribute for the at least one foreground object according to a first visual emphasis technique; and increasing the attribute for the background according to a second visual emphasis technique.

22. The method of claim 1, wherein the specified visual emphasis specifies one or more of:

luminance contrast of the at least one foreground object and/or the background;

chromatic contrast of the at least one foreground object and/or the background;

spatial frequency of the at least one foreground object and/or the background;

size of the at least one foreground object and/or features in the background;

flashing the at least one foreground object;

moving the at least one foreground object with respect to the background;

texture of the at least one foreground object and/or the background;

opacity of the at least one foreground object and/or the background;

positioning the at least one foreground object with respect to one or more other foreground objects and/or with respect to one or more features of the background; or attentional effects of one or more distracting features of the background;

wherein increasing the visual emphasis comprises:
increasing one or more others of the luminance contrast, the color contrast, the spatial frequency, the size, the flashing, the moving, the texture, the opacity, the positioning, or the reducing attentional effects; and wherein decreasing the visual emphasis comprises:
ceasing to modify at least one of said one or more of the luminance contrast, the color contrast, the spatial frequency, the size, the flashing, the moving, the texture, the opacity, the positioning, or the reducing attentional effects.

23. The method of claim 1, wherein said repeating comprises beginning with scenes of higher visual emphasis, wherein said modifying the specified visual emphasis comprises:

decreasing the visual emphasis if the participant responds correctly a specified number of times.

24. The method of claim 1, wherein said repeating comprises:

the participant progressing through a plurality of levels, with each successive level specifying lower visual emphasis.

25. The method of claim 1, wherein said modifying comprises:
decreasing the visual emphasis if the participant responds correctly; and
increasing the visual emphasis if the participant responds incorrectly.

26. The method of claim 25, wherein the visual emphasis comprises stimulus intensity, and wherein said modifying the visual stimulus composes adjusting the stimulus intensity.

27. The method of claim 26, wherein said adjusting the stimulus intensity is performed using a maximum likelihood procedure.

28. The method as recited in claim 27, wherein the maximum likelihood procedure comprises one or more of:

a QUEST (quick estimation by sequential testing) threshold procedure; or a ZEST (zippy estimation by sequential testing) threshold procedure.

29. The method of claim 28, wherein said adjusting the stimulus intensity comprises:

adjusting the stimulus intensity to approach and substantially maintain a specified success rate for the participant.

30. The method of claim 29, wherein said adjusting the stimulus intensity to approach and substantially maintain a specified success rate for the participant uses a single stair maximum likelihood procedure.

31. The method of claim 27, wherein said repeating comprises:

assessing the participant's performance a plurality of times during said repeating.

32. The method of claim 31, wherein said assessing the participant's performance a plurality of times is performed according to the maximum likelihood procedure.

33. The method of claim 32, wherein said assessing the participant's performance a plurality of times is performed using a 2-stair maximum likelihood procedure.

34. A non-transitory computer-readable memory medium that stores program instructions for enhancing cognition in a participant, utilizing a computing device to present visual stimuli for training, and to receive responses from the participant, wherein the program instructions are executable by a processor to perform:

providing one or more scenes, each having a background and at least one foreground object, wherein the one or more scenes are available for visual presentation to the participant;

visually presenting a scene from the one or more scenes to the participant, wherein said visually presenting comprises visually presenting the at least one foreground object and/or the background with a specified visual emphasis that visually distinguishes the at least one foreground object with respect to the background;

requiring the participant to respond to the scene;

determining whether the participant responded correctly;

modifying the specified visual emphasis based on said determining, wherein said modifying the specified visual emphasis comprises adjusting the degree of visual emphasis according to one or more visual emphasis techniques; and repeating said visually presenting, said requiring, and said determining one or more times in an iterative manner to improve the participant's cognition.

35. The non-transitory memory medium of claim 34, wherein said modifying the specified visual emphasis comprises one or more of:

modifying the visual emphasis of the at least one foreground object and/or the background to modify the visual emphasis; or selecting a different at least one foreground object and/or a different background for the scene to modify the visual emphasis.

* * * * *